(12) United States Patent
Kim

(10) Patent No.: US 11,040,074 B2
(45) Date of Patent: Jun. 22, 2021

(54) **NANOVESICLE DERIVED FROM *PROTEUS* GENUS BACTERIA, AND USE THEREOF**

(71) Applicant: MD HEALTHCARE INC., Seoul (KR)

(72) Inventor: Yoon-Keun Kim, Paju-si (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 16/362,176

(22) Filed: Mar. 22, 2019

(65) Prior Publication Data
US 2019/0209624 A1 Jul. 11, 2019

Related U.S. Application Data

(63) Continuation of application No. PCT/KR2018/007144, filed on Jun. 25, 2018.

(30) Foreign Application Priority Data

Jun. 30, 2017 (KR) .......................... 10-2017-0083047
Jun. 22, 2018 (KR) .......................... 10-2018-0072307

(51) Int. Cl.
| | | |
|---|---|---|
| *A61K 39/385* | (2006.01) | |
| *A61K 39/02* | (2006.01) | |
| *A61K 39/00* | (2006.01) | |
| *A61K 39/38* | (2006.01) | |
| *A61K 35/74* | (2015.01) | |
| *A61K 9/00* | (2006.01) | |
| *C12Q 1/689* | (2018.01) | |
| *A61P 25/28* | (2006.01) | |
| *A61K 9/127* | (2006.01) | |
| *A61P 35/00* | (2006.01) | |
| *A61P 29/00* | (2006.01) | |
| *C12Q 1/6886* | (2018.01) | |
| *A61K 38/00* | (2006.01) | |

(52) U.S. Cl.
CPC ............ *A61K 35/74* (2013.01); *A61K 9/0053* (2013.01); *A61K 9/0073* (2013.01); *A61K 9/127* (2013.01); *A61P 25/28* (2018.01); *A61P 29/00* (2018.01); *A61P 35/00* (2018.01); *C12Q 1/689* (2013.01); *C12Q 1/6886* (2013.01); *A61K 38/00* (2013.01); *A61K 39/00* (2013.01); *A61K 2039/6037* (2013.01)

(58) Field of Classification Search
CPC .................................................... A61K 35/74
See application file for complete search history.

(56) References Cited

U.S. PATENT DOCUMENTS

| 2010/0233195 A1* | 9/2010 | Delisa ................ C12N 15/1037 424/184.1 |
| 2012/0196764 A1 | 8/2012 | Zhang et al. |
| 2013/0121968 A1* | 5/2013 | Quay ....................... G06F 19/34 424/93.4 |

FOREIGN PATENT DOCUMENTS

| KR | 10-2016-0073157 A | 6/2016 |
| WO | 2011/027990 A2 | 3/2011 |
| WO | 2016/201519 A1 | 12/2016 |

OTHER PUBLICATIONS

Kuehn et al., Genes & Development, 2005; 19:2645-2655 (Year: 2005).*
Ha et al., Acta Pharmaceutica Sinica B, 2016; 6(4): 287-296 (Year: 2016).*
Jeyaram et al., AAPS J, 2019; 20(1): 1-13 (Year: 2019).*
Mizuno et al., Cancer Research, 1968; 28: 1531-1537 (Year: 1968).*
Asthma, Mayo Clinic, https://www.mayoclinic.org/diseases-conditions/asthma/diagnosis-treatment/drc-20369660, accessed Oct. 22, 2020 (Year: 2020).*
Stroke, Mayo Clinic, https://www.mayoclinic.org/diseases-conditions/stroke/diagnosis-treatment/drc-20350119 (Year: 2020).*
Depression, Mayo clinic, https://www.mayoclinic.org/diseases-conditions/depression/diagnosis-treatment/drc-20356013 (Year: 2020).*
Murata et al., "Oncolytic Effect of Proteus Mirabilis upon Tumor Bearing Animal", Life Sciences, 1965, vol. 4, pp. 1055-1067.
Von Rhein et al., "Occurrence and characteristics of the cytolysin A gene in Shigella strains and other members of the family Enterobacteriaceae", FEMS Microbiol Lett (2008); 143-145.
Extended European search report for corresponding EP Application No. 18825252.2, dated Feb. 18, 2021, 12 pages.
Bitto et al., "The Therapeutic Benefit of Bacterial Membrane Vesicles", International Journal of Molecular Sciences, 2017, vol. 18, No. 6, 15 Pages.
Gutman, "Cases of bronchial asthma treated with Morgan and Proteus", J Am Inst Homeopath, 1966, vol. 59, No. 1, p. 46.
Hilty et al., "Disordered microbial communities in asthmatic airways", PLOS One, 2010, vol. 5, Issue 1, e8578, 9 Pages.

(Continued)

*Primary Examiner* — Gary B Nickol
*Assistant Examiner* — Lakia J Jackson-Tongue
(74) *Attorney, Agent, or Firm* — Vorys, Sater, Seymour & Pease LLP; Mih Suhn Koh

(57) ABSTRACT

Provided are vesicles derived from bacteria belonging to the genus *Proteus* and a use thereof. The inventors of the present invention experimentally confirmed that the vesicles was significantly reduced in samples of patients with cancers, allergic-respiratory diseases, cardiovascular diseases, metabolic diseases, or neuropsychiatric diseases, as compared to that of normal people, and the vesicles inhibited the secretion of inflammatory mediators due to pathogenic vesicles and also exhibited anticancer efficacy. Therefore, it is anticipated that the vesicles derived from bacteria belonging to the genus *Proteus*, according to the present invention, may be usefully used for the development of a method of diagnosing cancer, cardiovascular diseases, metabolic diseases, neuropsychiatric diseases, allergic-respiratory diseases, and inflammatory bowel diseases, and a composition for prevention, treatment, and/or alleviation.

4 Claims, 25 Drawing Sheets

Specification includes a Sequence Listing.

(56) References Cited

OTHER PUBLICATIONS

Jiang et al., "Altered fecal microbiota composition in patients with major depressive disorder", Brain, Behavior, and Immunity, 2015, vol. 48, pp. 186-194.
Kim et al., "Bacterial outer membrane vesicles suppress tumor by interferon-[gamma]-mediated antitumor response", Nature Communications, 2017, vol. 8, No. 1, 9 Pages.
Sampson et al., "Gut Microbiota Regulate Motor Deficits and Neuroinflammation in a Model of Parkinson's Disease", Cell, 2016, vol. 167, No. 6, pp. 1469-1480.
Zhang et al., "Proteus mirabilis inhibits cancer growth and pulmonary metastasis in a mouse breast cancer model", PLOS ONE, 2017, vol. 12, No. 12, 20 Pages.

\* cited by examiner

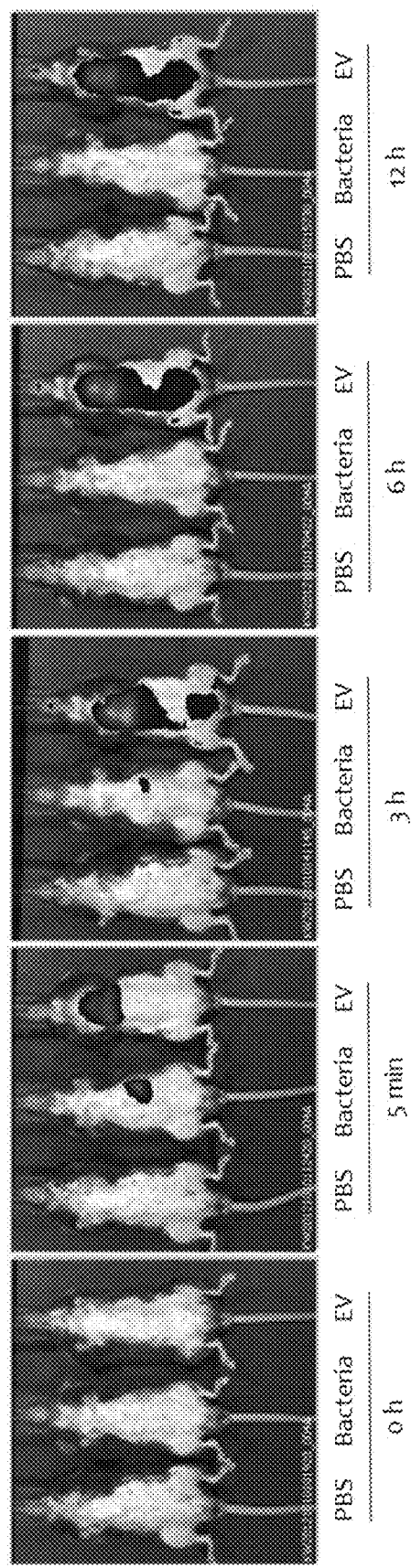
[Fig. 1A]

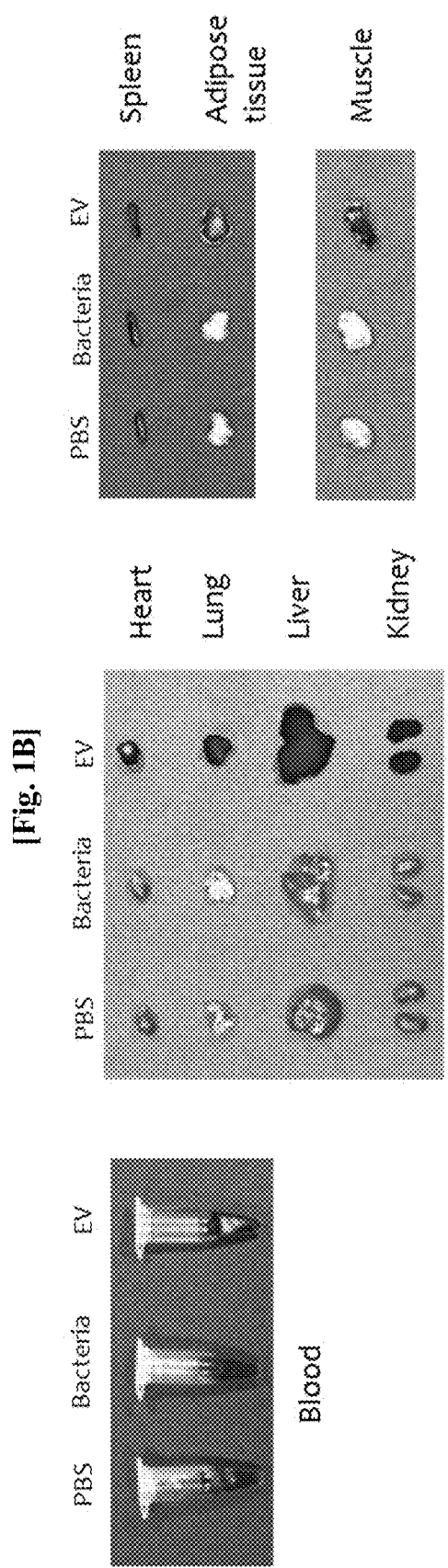

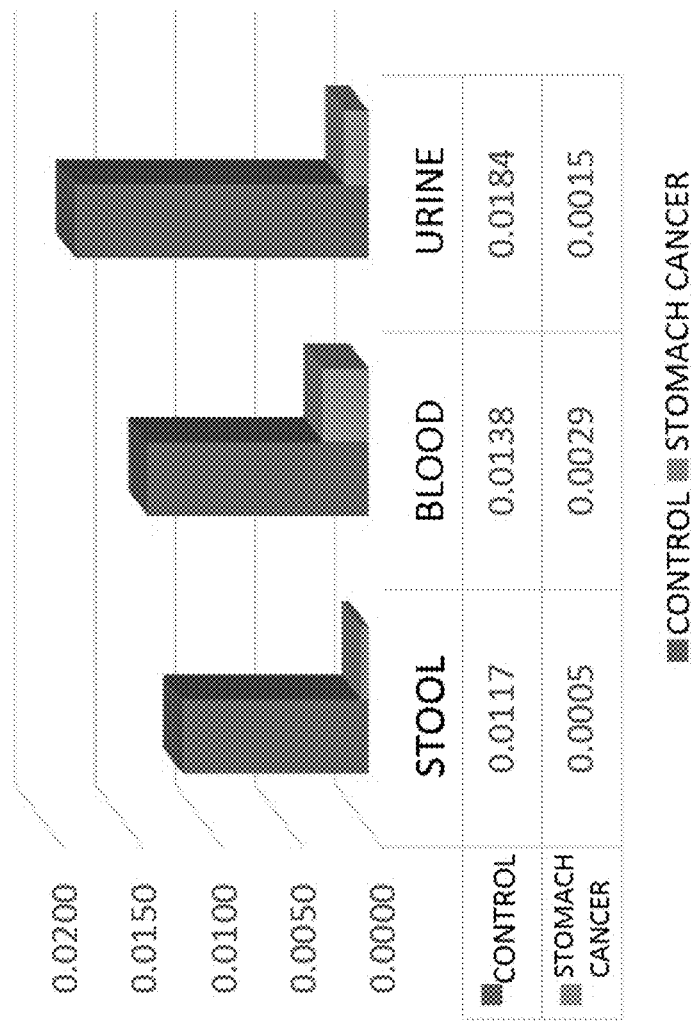
[Fig. 2]

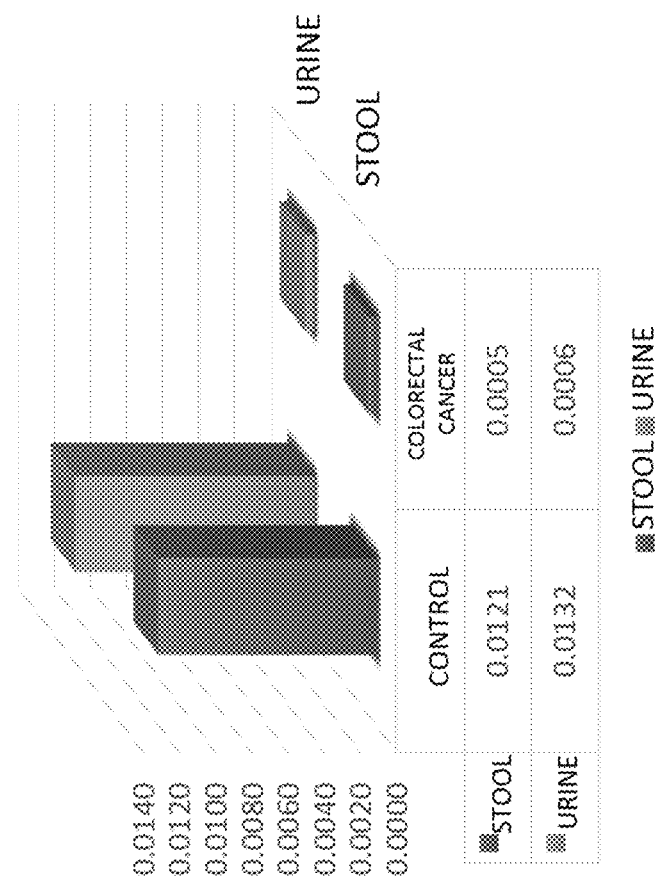

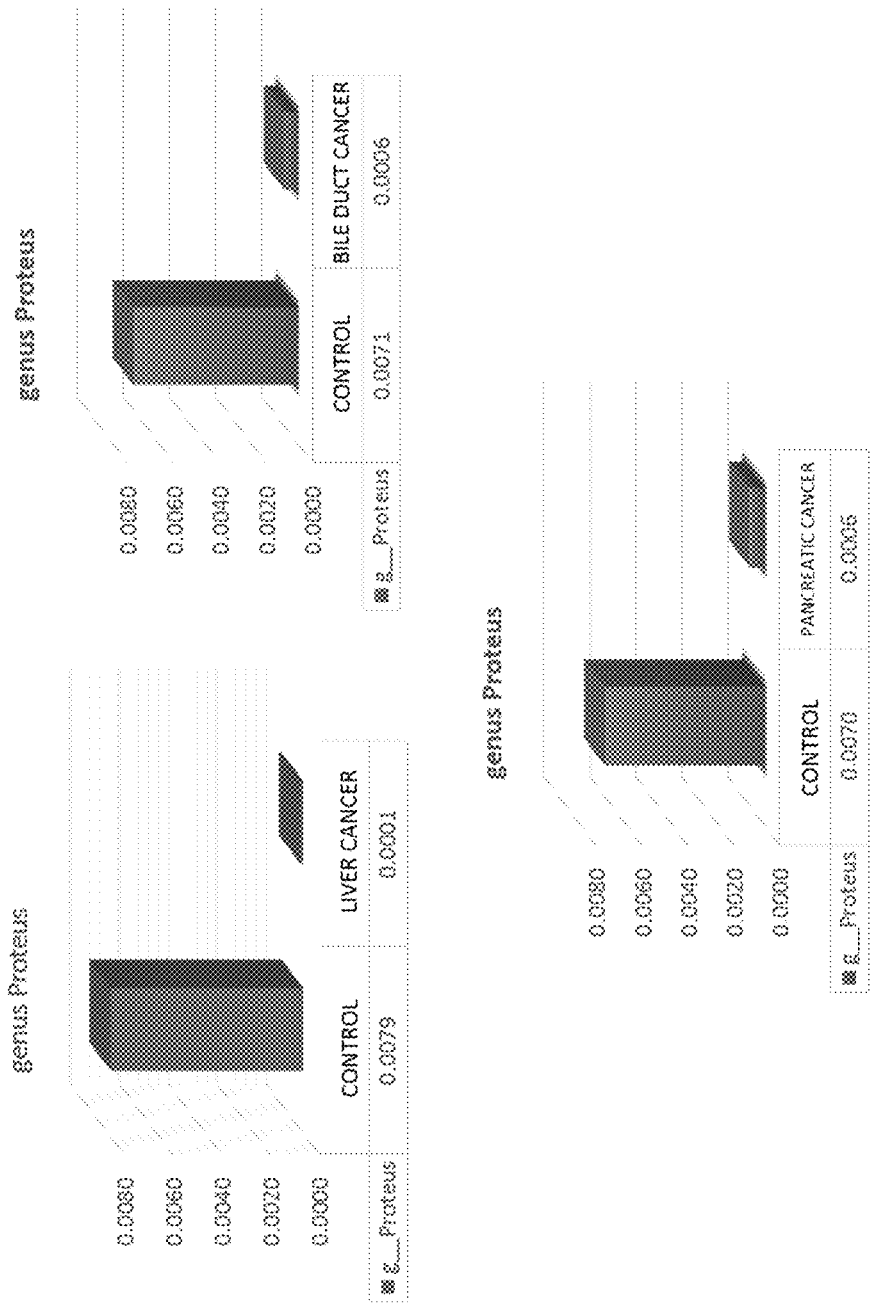

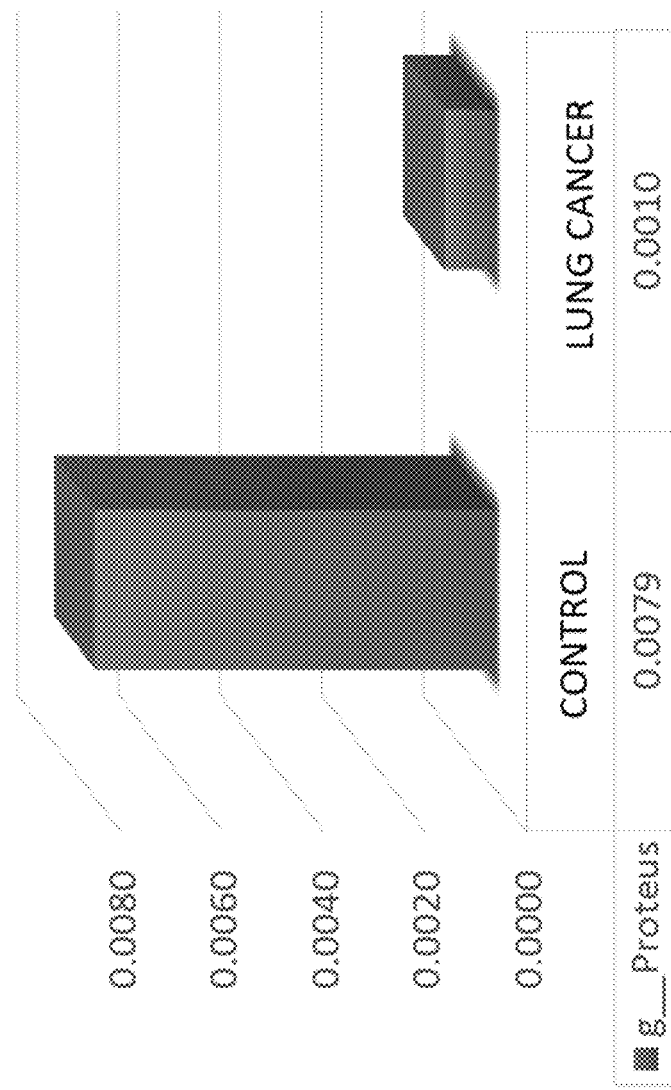

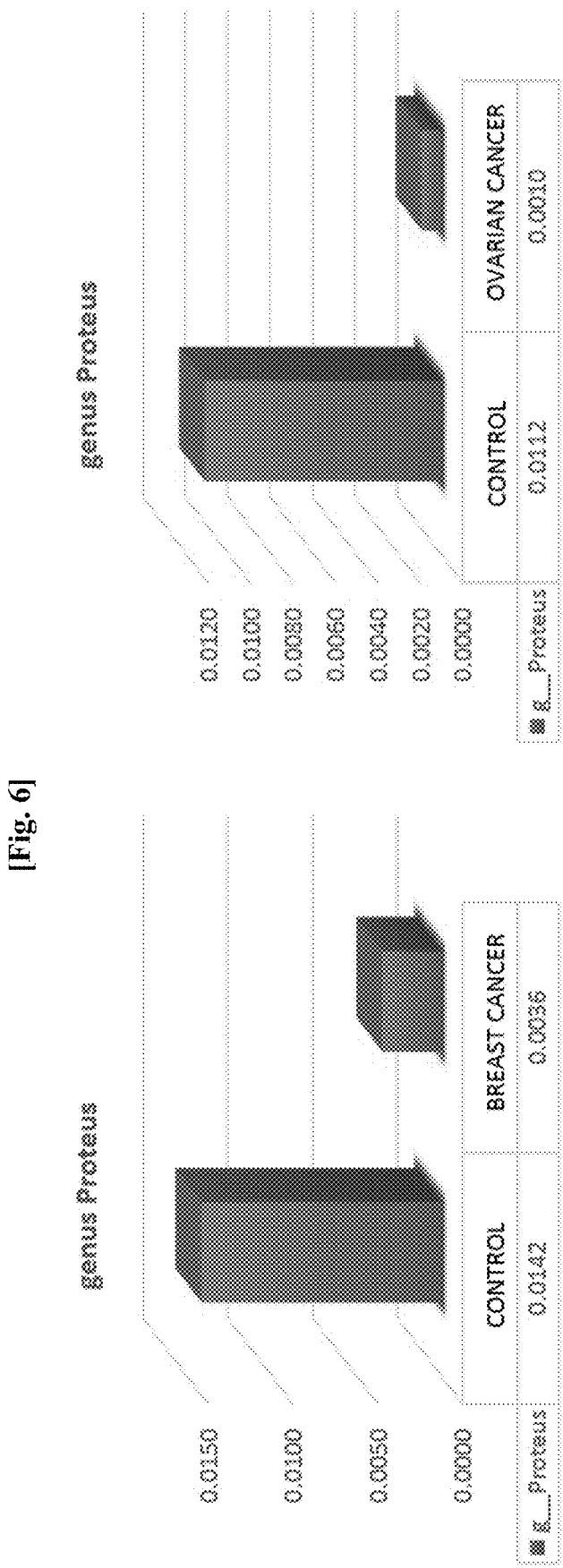
[Fig. 6]

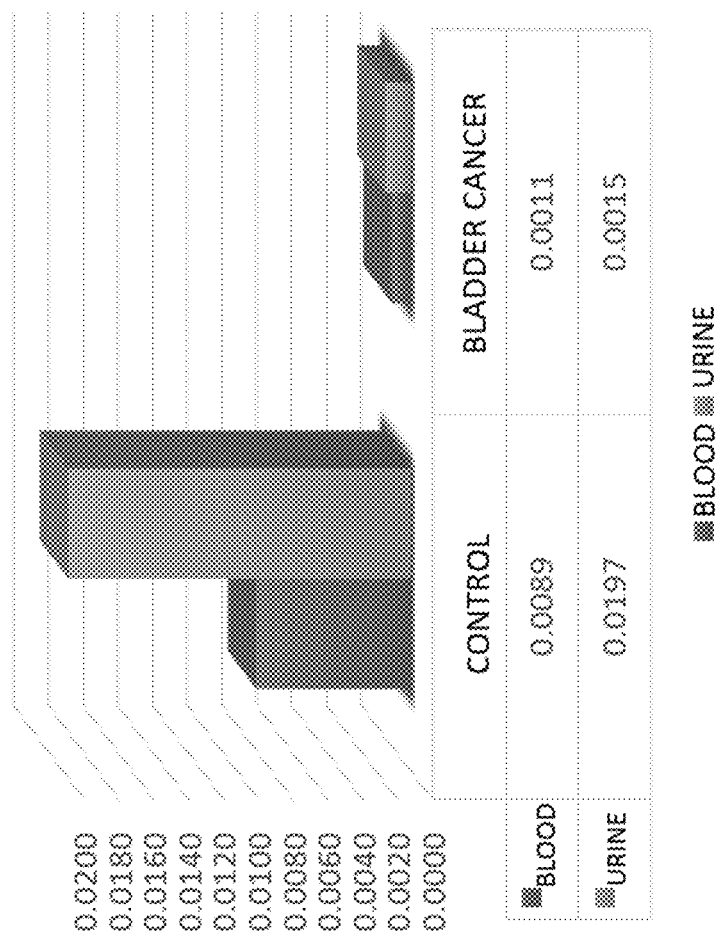

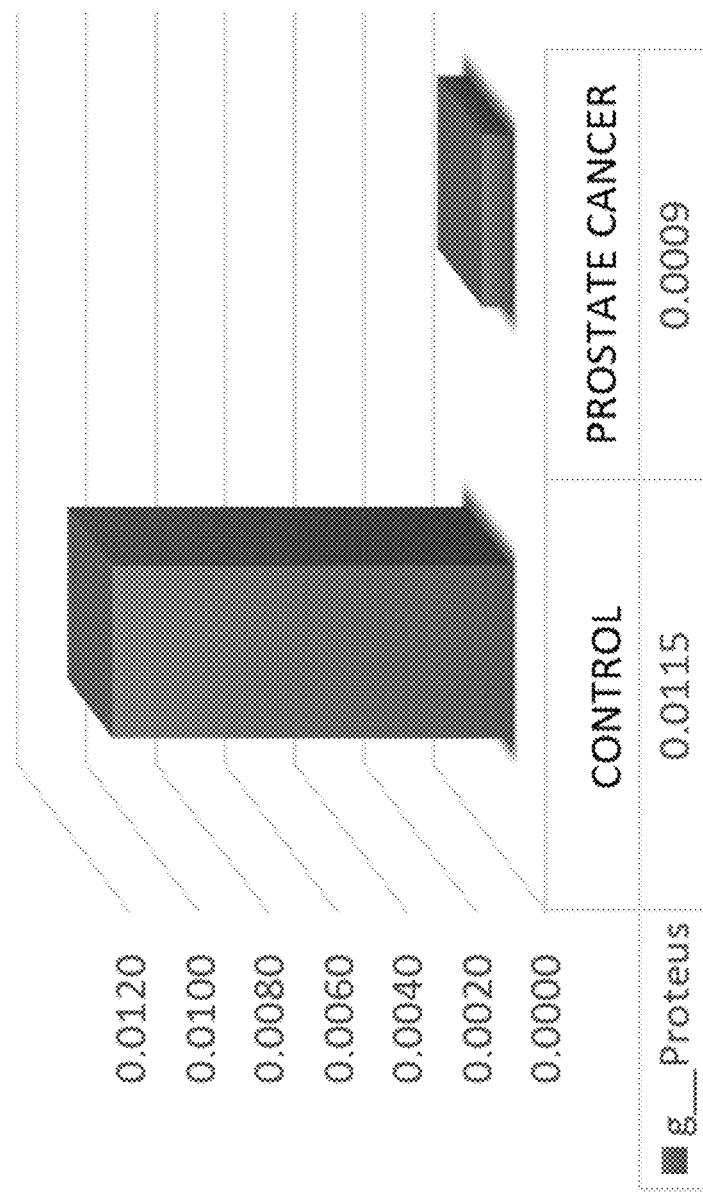
[Fig. 8]

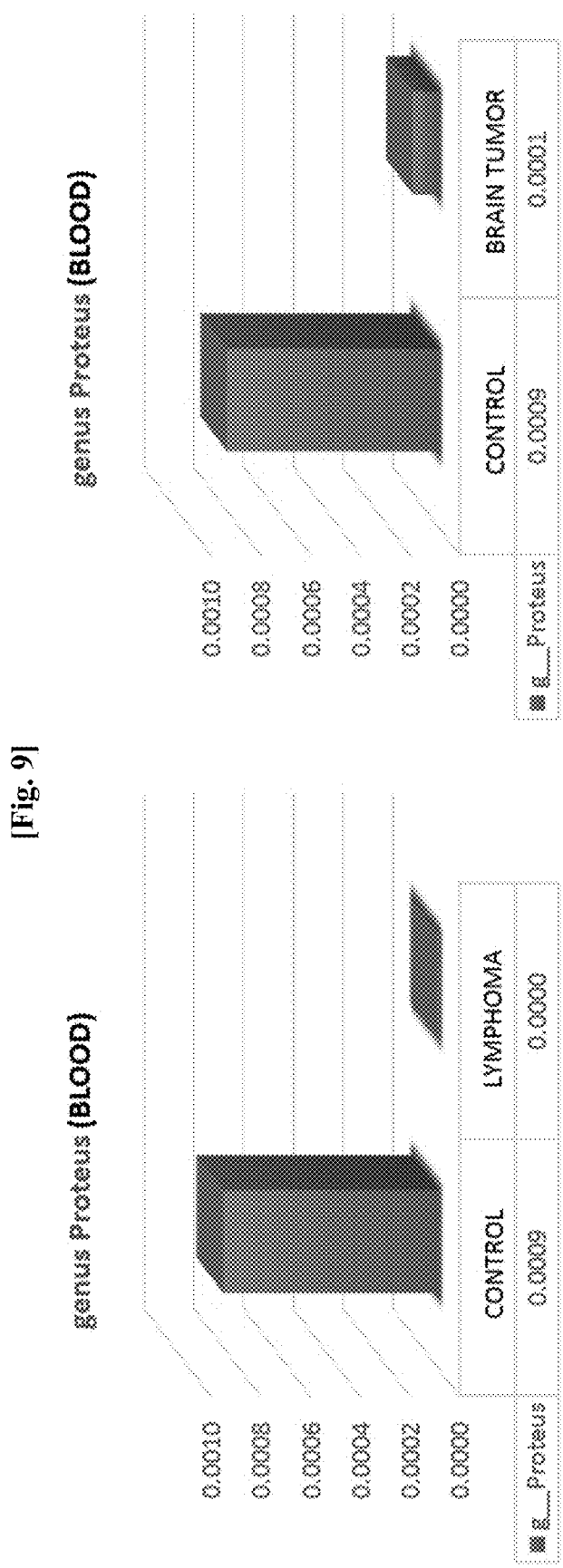
[Fig. 9]

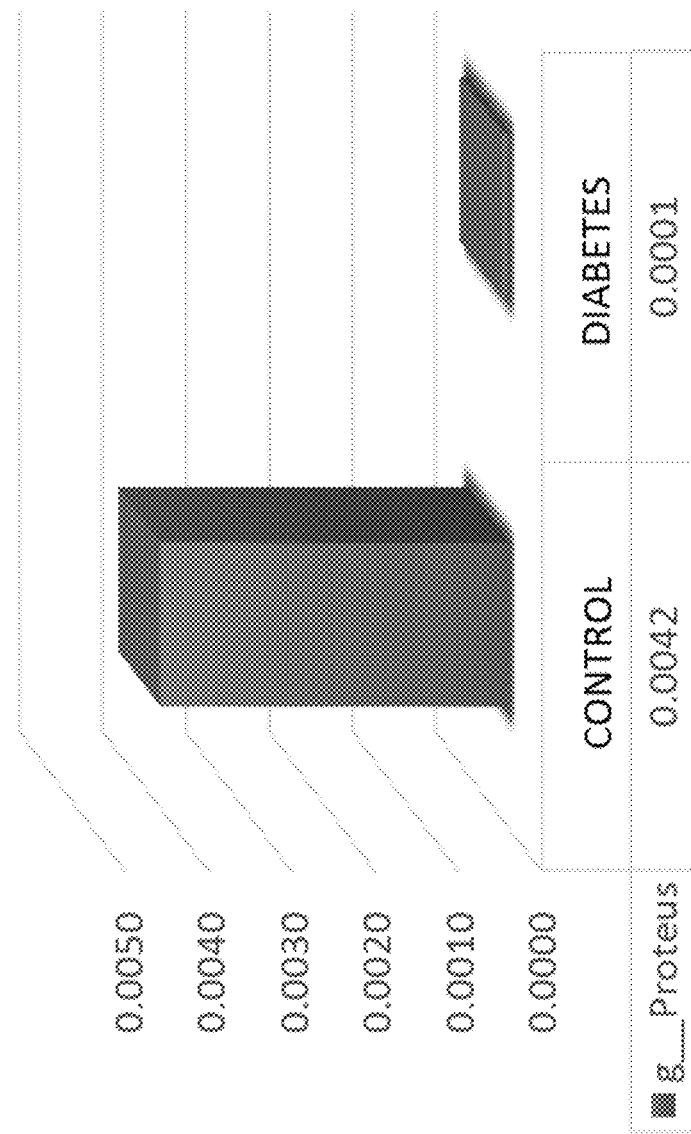

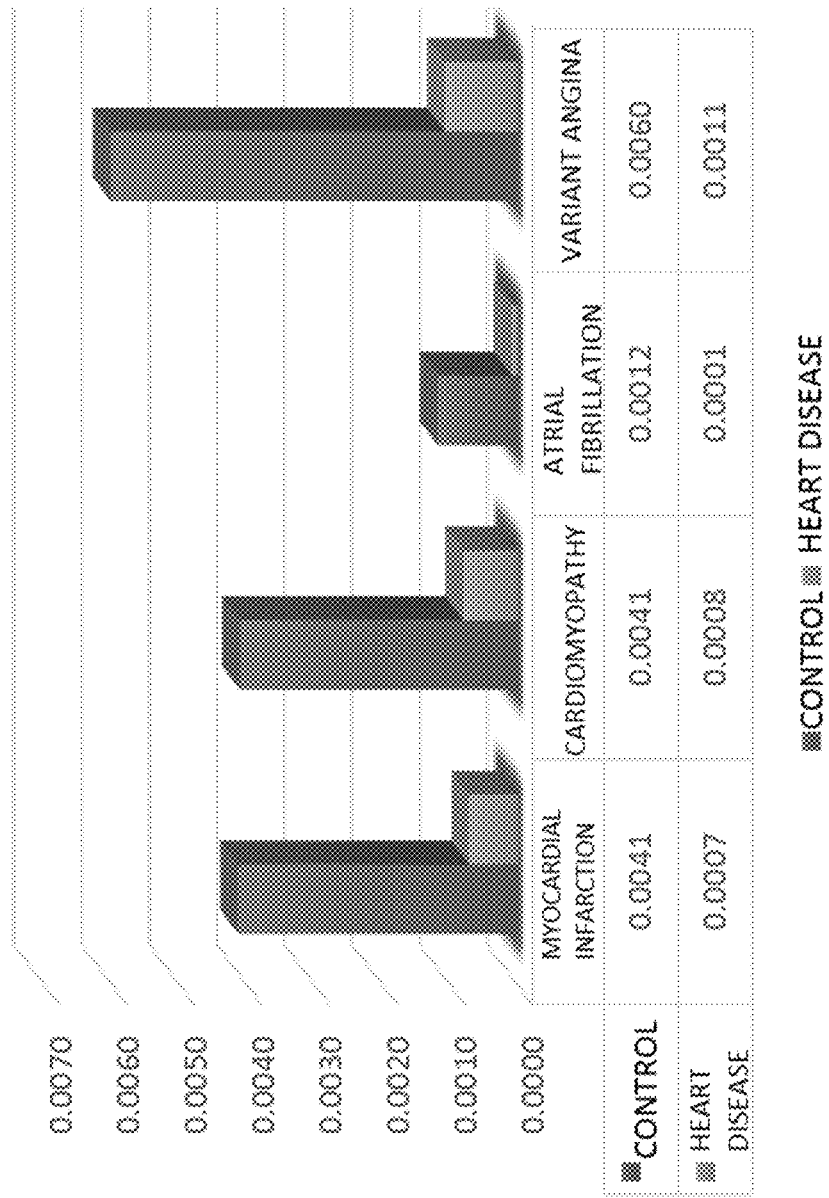

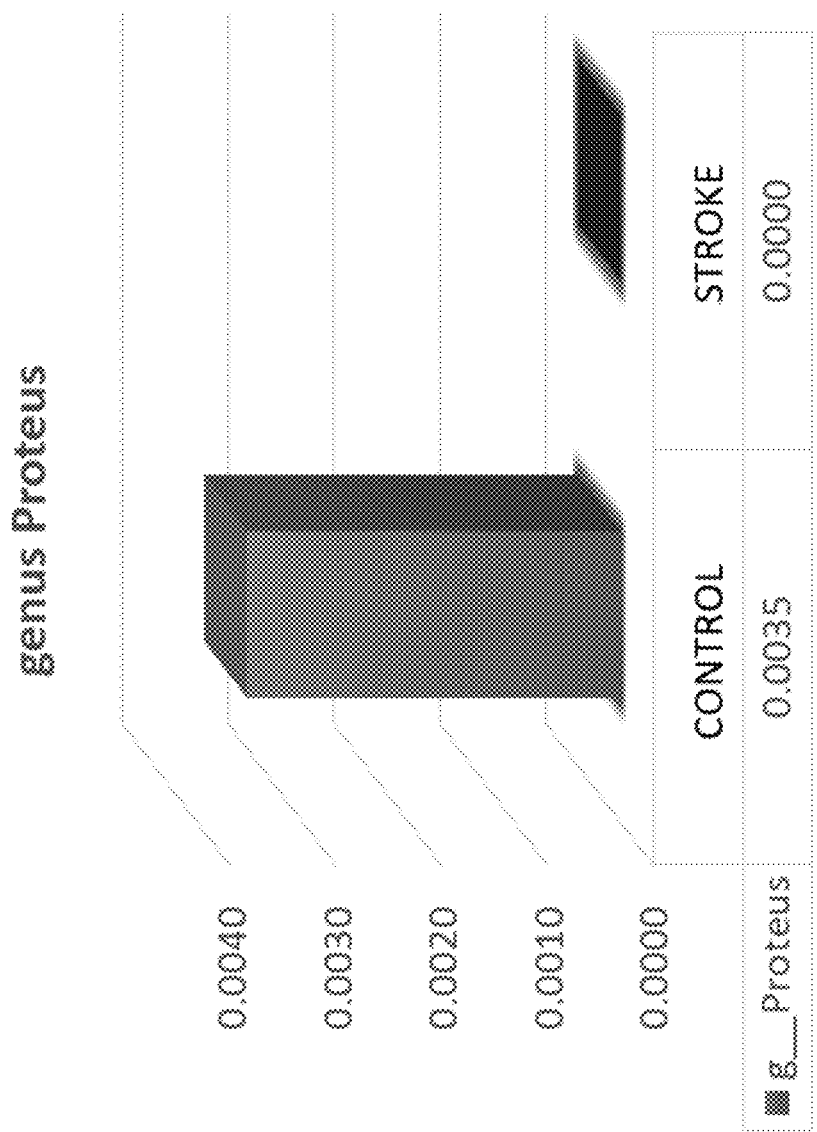
[Fig. 12]

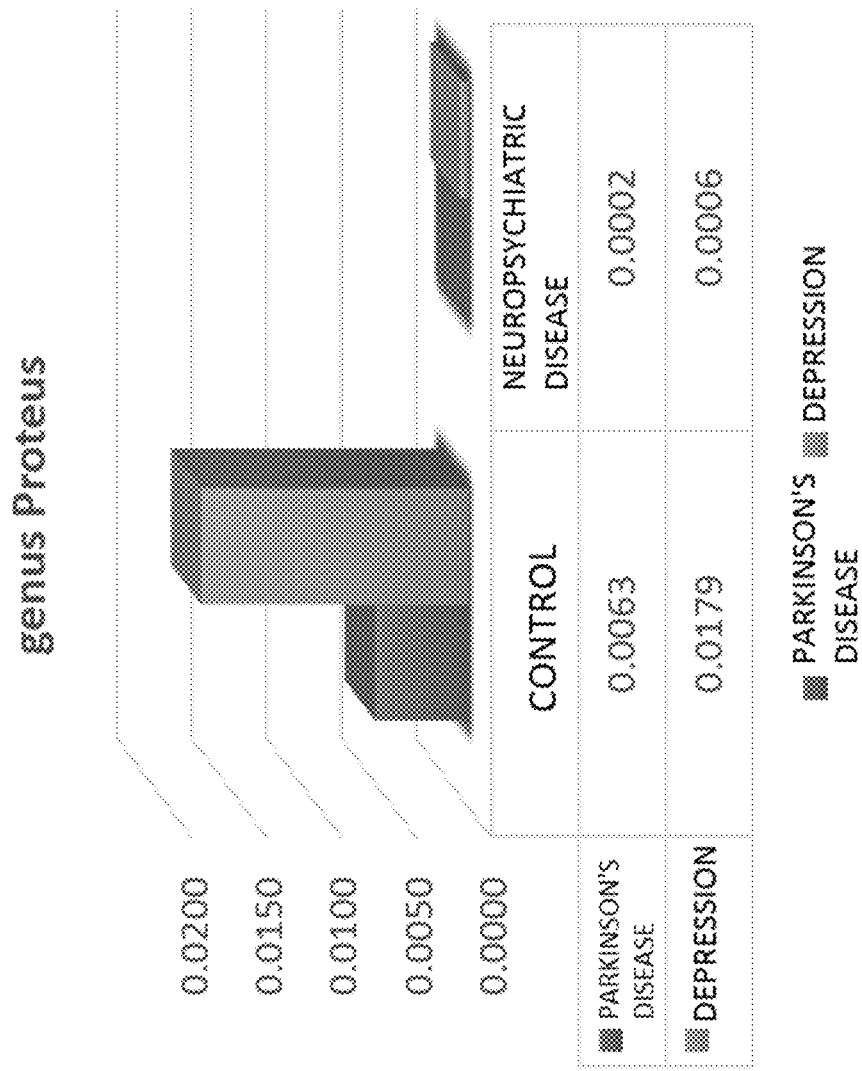

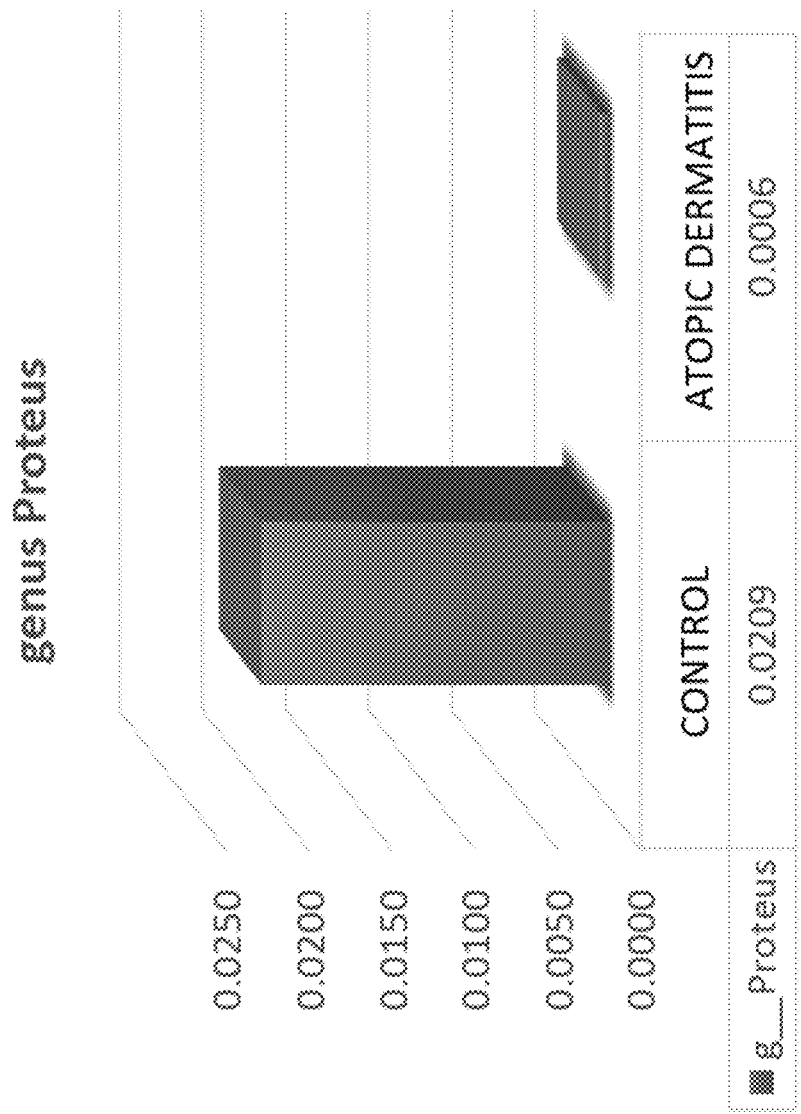
[Fig. 14]

[Fig. 15]
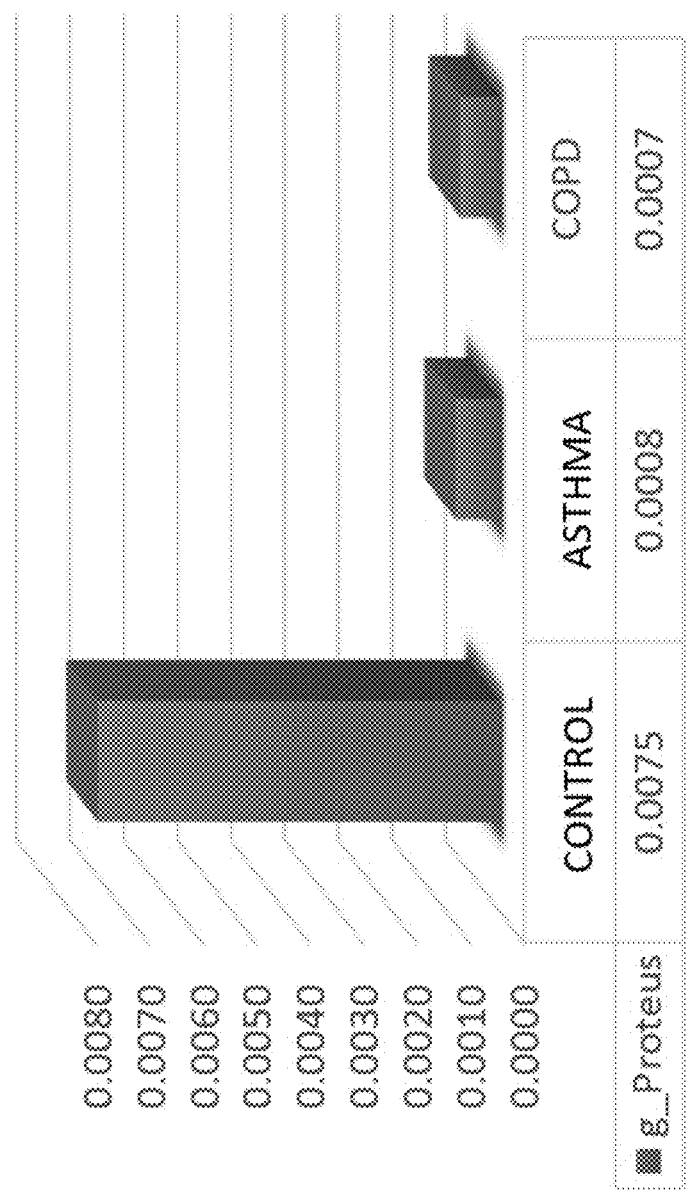

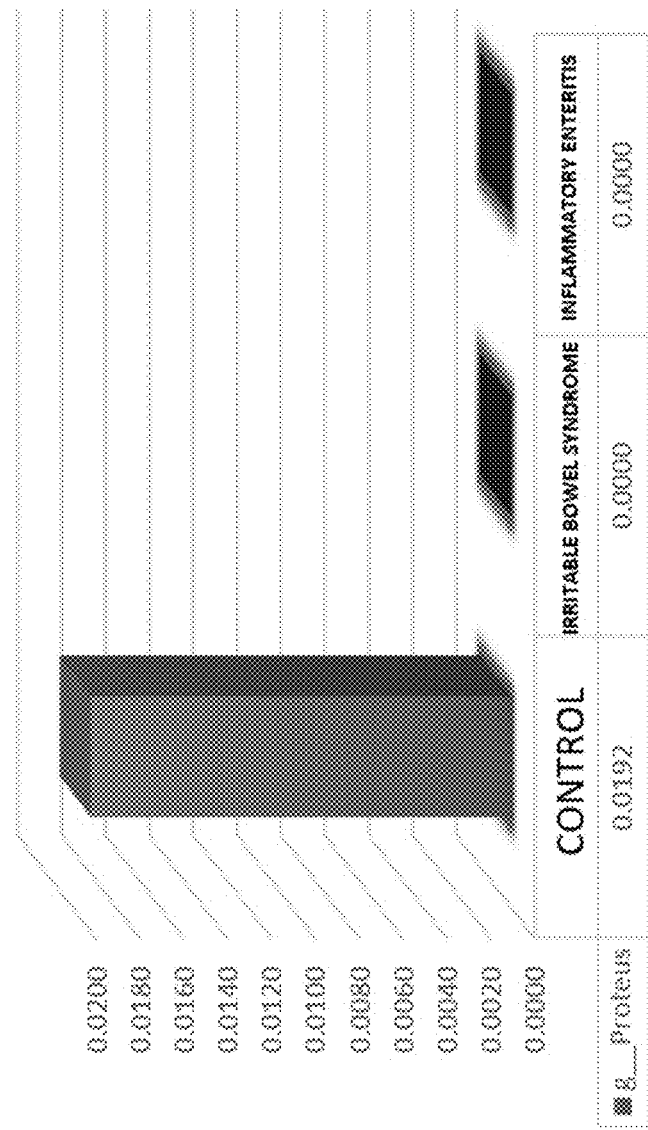

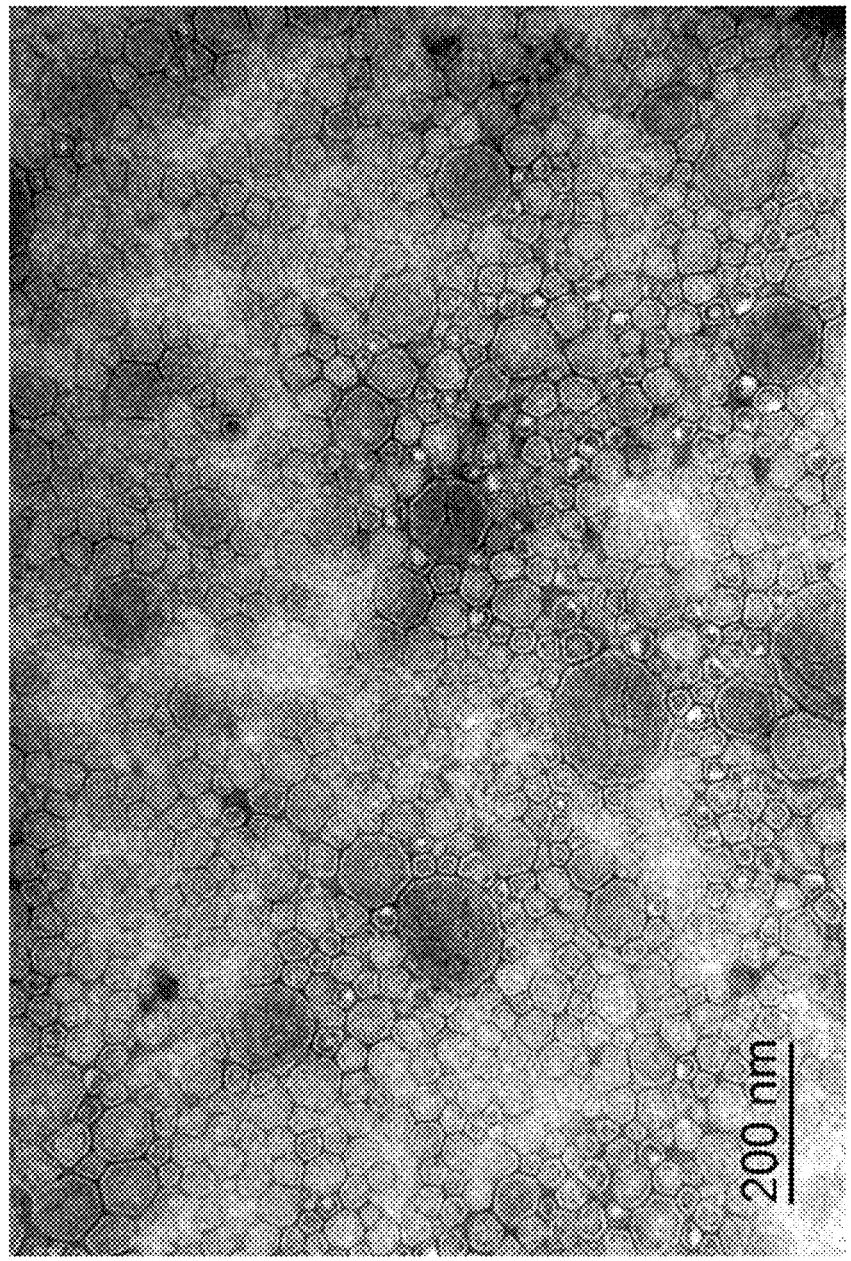
[Fig. 17A]

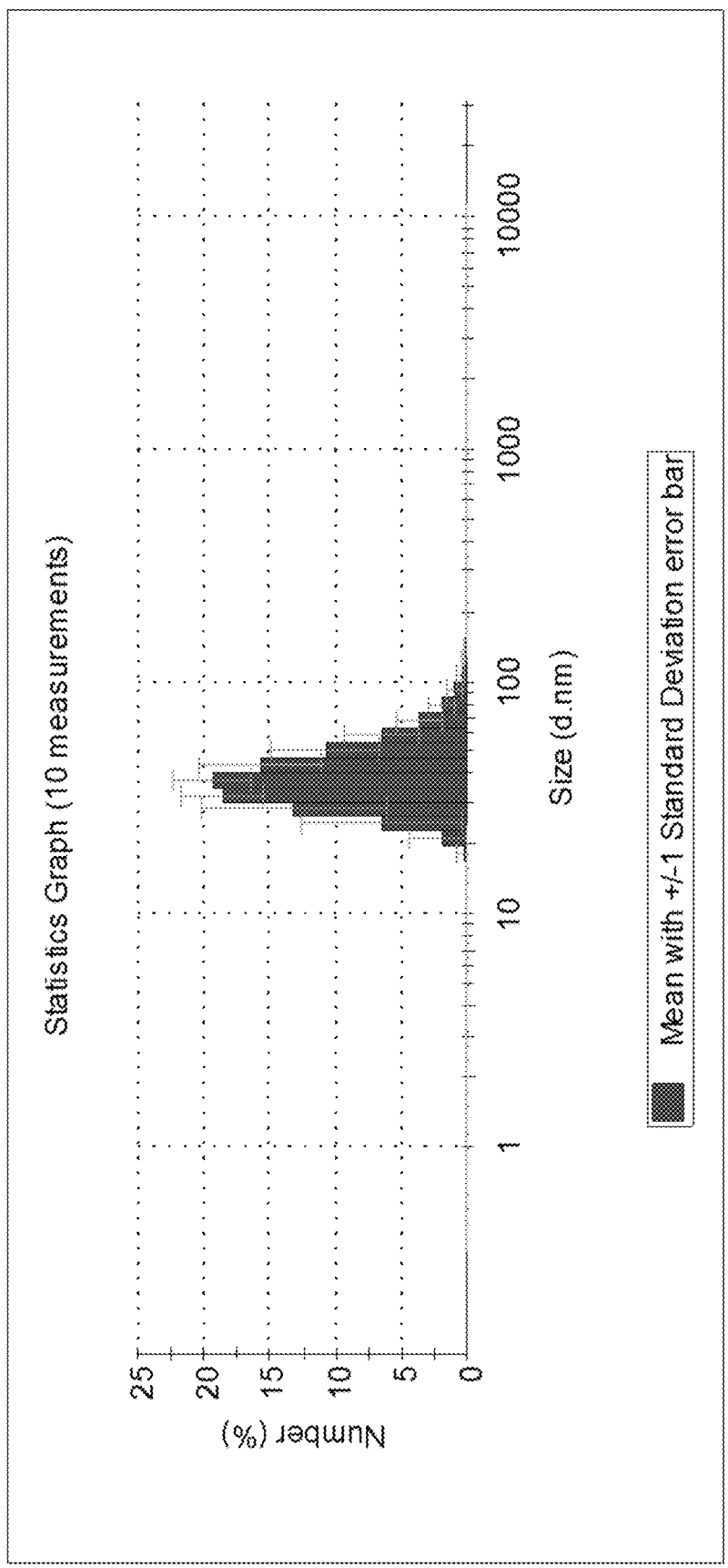
[Fig. 17B]

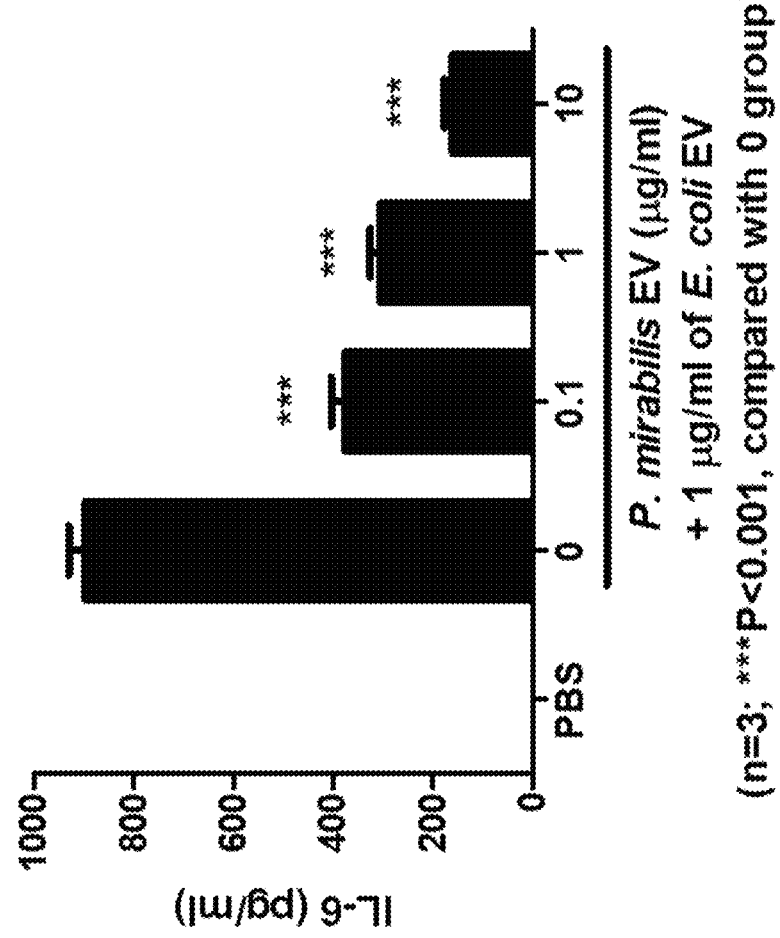
[Fig. 18A]

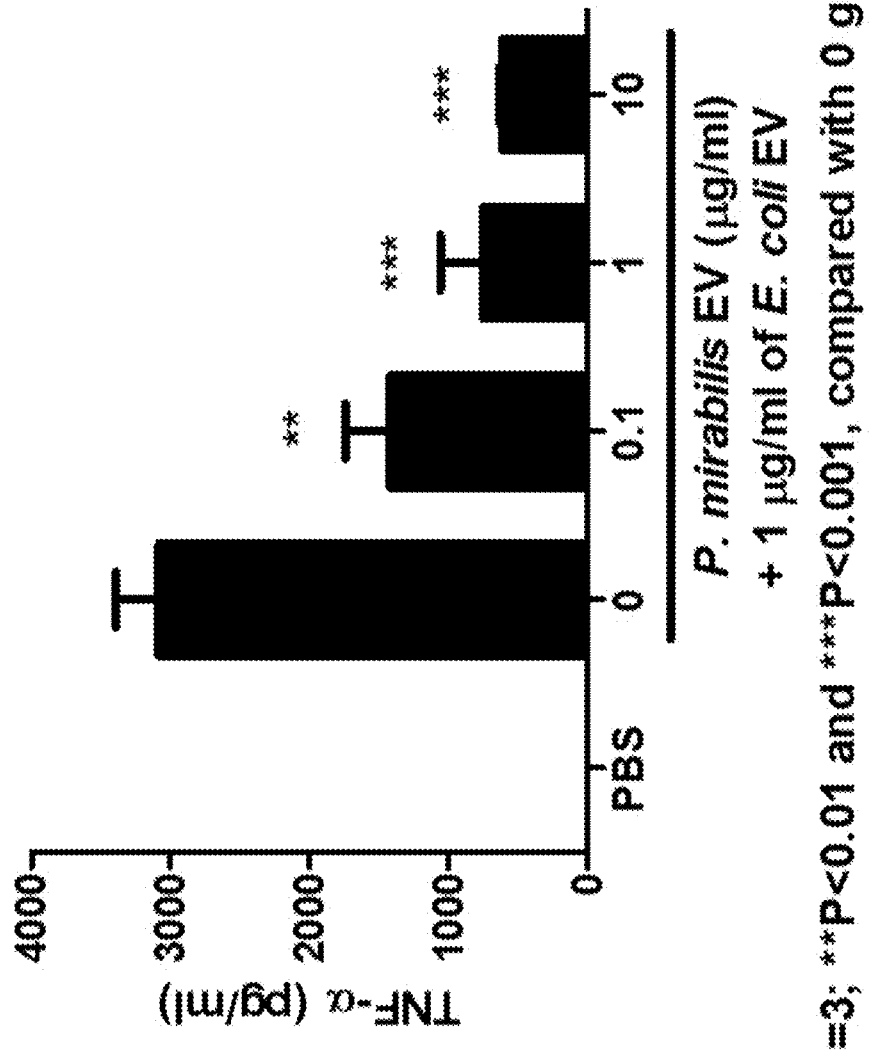

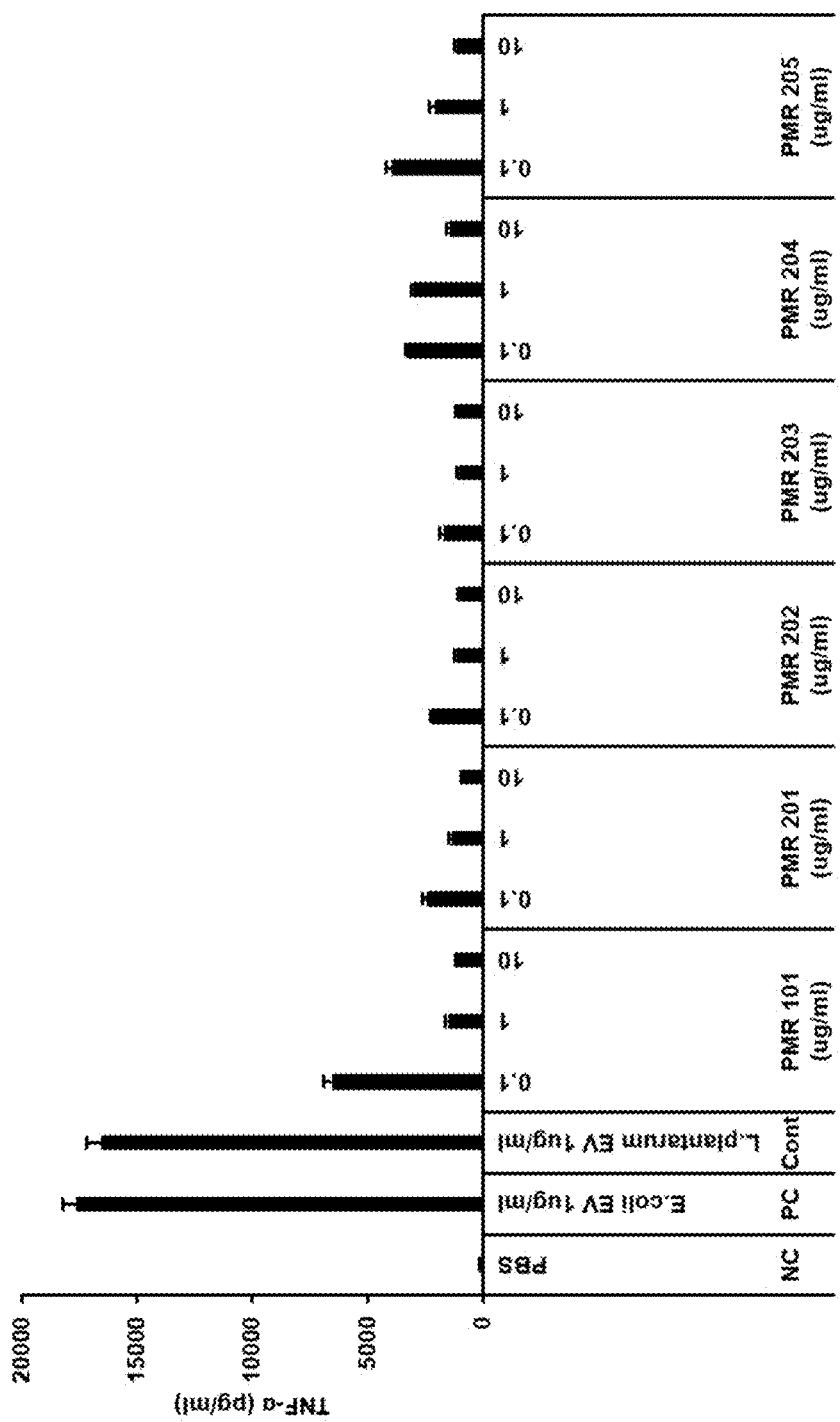
[Fig. 19]

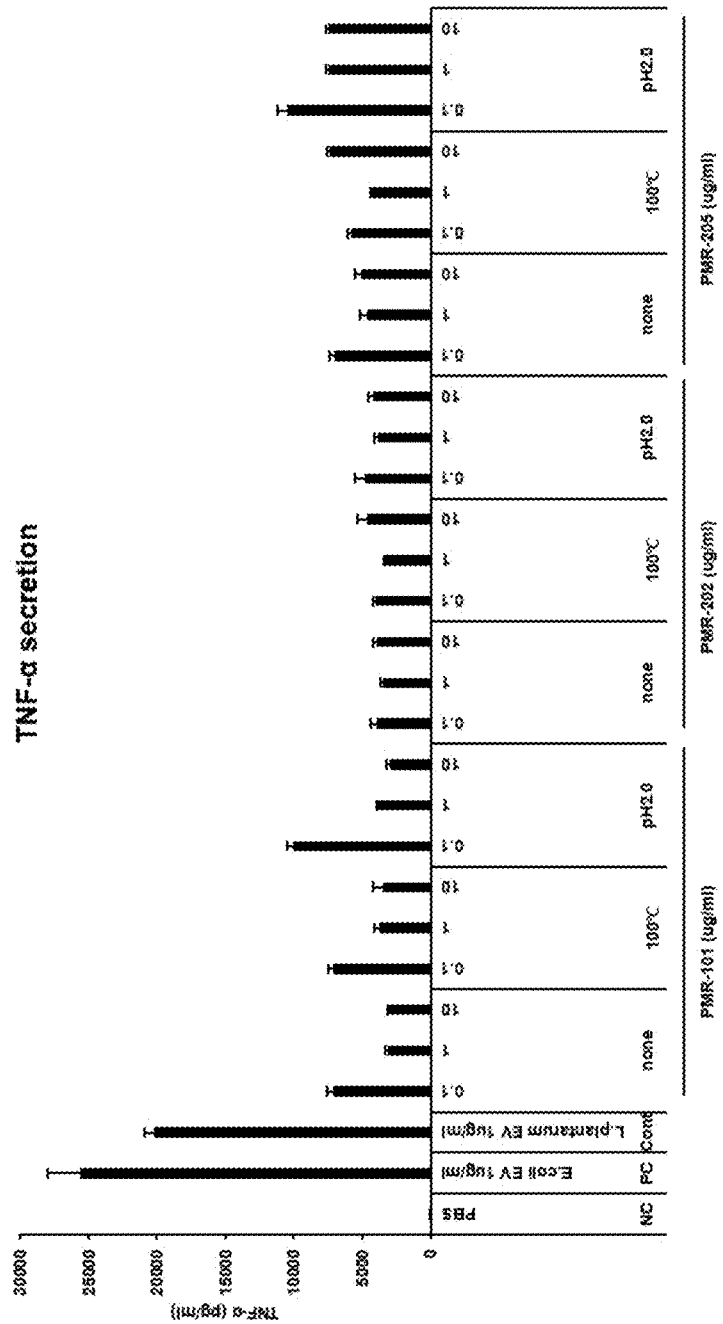

[Fig. 21A]
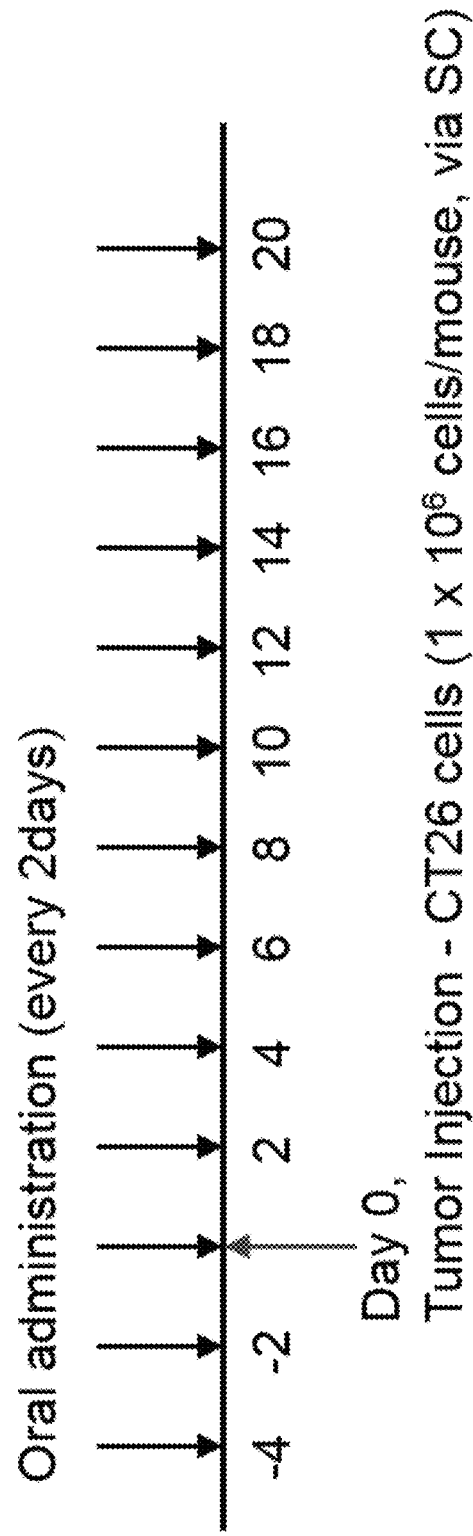

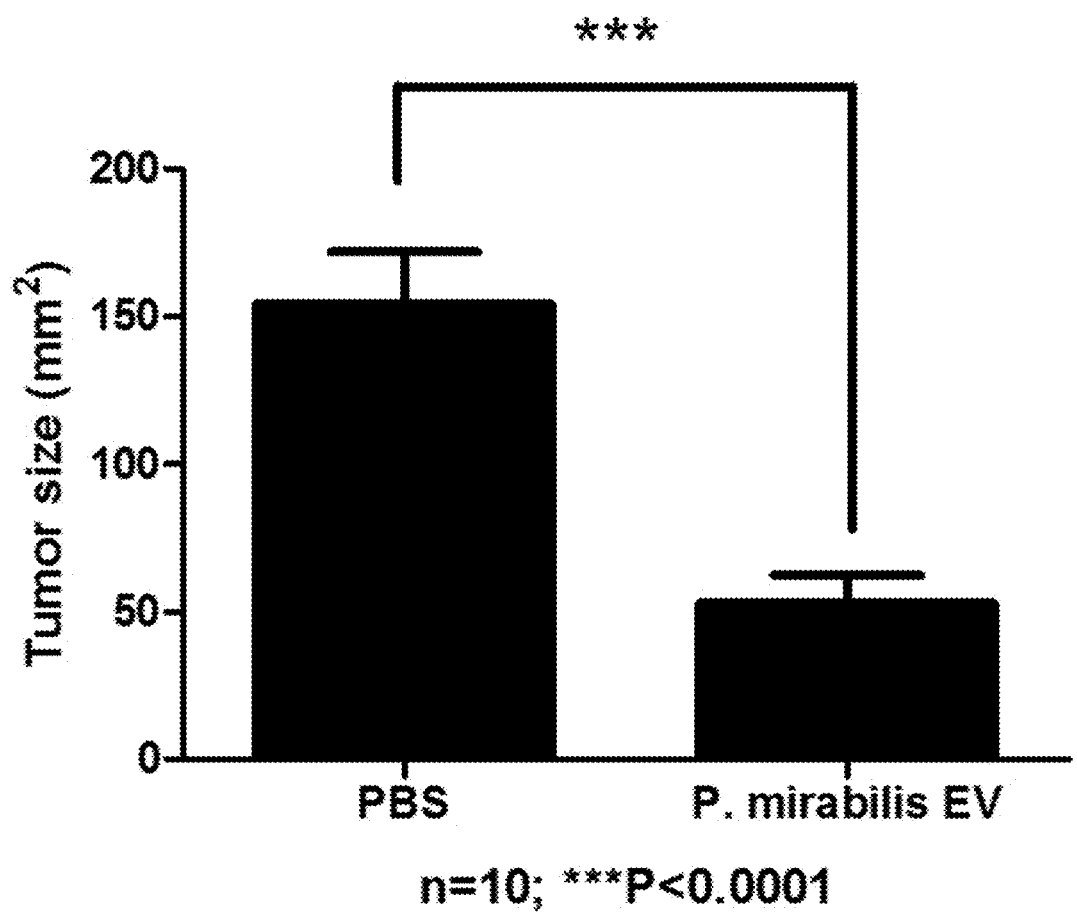
[Fig. 21B]

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)
<223> OTHER INFORMATION: a, c, g or t

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc       55

NANOVESICLE DERIVED FROM *PROTEUS* GENUS BACTERIA, AND USE THEREOF

CROSS-REFERENCE TO RELATED APPLICATION

This application is a continuation of PCT/KR2018/007144, filed Jun. 25, 2018, which claims the benefit of priority from Korean Patent Application No. 10-2017-0083047, filed Jun. 30, 2017 and Korean Patent Application No. 10-2018-0072307, filed Jun. 22, 2018, the contents of each of which are incorporated herein by reference in its entirety.

SEQUENCE LISTING

The Sequence Listing submitted in text format (.txt) filed on Mar. 22, 2019, named "SequenceListing.txt", created on Mar. 22, 2019 (719 bytes), is incorporated herein by reference.

TECHNICAL FIELD

The present invention relates to nanovesicles derived from bacteria belonging to the genus *Proteus* and a use thereof, and more particularly, to a method of diagnosing cancers, cardiovascular diseases, metabolic diseases, neuropsychiatric diseases, allergic-respiratory diseases, and inflammatory bowel diseases, which are characterized by chronic inflammation, by using nanovesicles derived from bacteria belonging to the genus *Proteus*, and a preventive or therapeutic composition including the nanovesicles.

BACKGROUND ART

In the $21^{st}$ century, the importance of acute infectious diseases, which have been recognized as epidemics in the past, has become less important. On the other hand, a disease pattern has been changed such that chronic diseases accompanied by immune dysfunction occurring due to incompatibility between humans and microbiomes are considered as a major disease that determines the quality of life and human lifespan. In the $21^{st}$ century, intractable chronic diseases are characterized by chronic inflammatory responses caused by immune dysfunction due to repetitive exposure to causative factors according to lifestyle changes, and as examples thereof, cancer, cardiovascular diseases, metabolic diseases, neuropsychiatric diseases, allergic-respiratory diseases, inflammatory bowel diseases, and the like are becoming serious problems in public health.

As immune responses to bacteria-derived causative factors, a T helper 17 (Th17) immune response characterized by the secretion of interleukin-17 cytokines is important, and an innate immune response such as the secretion of interleukin-6 (IL-6) due to bacterial factors plays a crucial role in differentiation into Th17 cells. In addition, it is known that inflammation occurs upon exposure to bacterial causative factors, and in this process, inflammatory mediators such as tumor necrosis factor-α (TNF-α) are secreted, thus causing the onset of cancer, cardiovascular diseases, metabolic diseases, neuropsychiatric diseases, allergic-respiratory diseases, inflammatory bowel diseases, and the like.

It is known that the number of microorganisms symbiotically living in the human body is 100 trillion which is 10 times that of human cells, and the number of genes of microorganisms exceeds 100 times that of humans. Bacteria and archaea symbiotically living in the human body secrete nanometer-sized vesicles to exchange information about genes, proteins, and the like with other cells. The mucous membranes form a physical barrier membrane that does not allow particles with a size of 200 nm or more to pass therethrough, and thus bacteria symbiotically living in the mucous membranes are unable to pass therethrough, but bacteria-derived vesicles have a size of approximately 100 nm or less and thus relatively freely pass through the mucous membranes and are absorbed into epithelial cells, thus inducing inflammatory responses, and are also absorbed into the human body through lymphatic vessels. Bacteria-derived vesicles that are locally secreted from bacteria symbiotically living in the human body are absorbed into epithelial cells of the mucous membrane to thereby induce a local inflammatory response, and pathogenic bacteria-derived vesicles absorbed into the human body are distributed to respective organs through blood to thereby increase inflammatory responses in the organs, thus aggravating diseases.

Bacteria belonging to the genus *Proteus*, which are anaerobic Gram-negative bacilli, convert urea into ammonia through a urease to thereby alkalize urine. Among the above bacteria, *Proteus mirabilis*, which is known as a pathogenic bacterium, accounts for 90% of the cases of infection with bacteria belonging to the genus *Proteus* in humans. The bacteria belonging to the genus *Proteus* are known to symbiotically live in the digestive organs of humans and also widely inhabit an environment such as soil, water, and the like.

Meanwhile, inventions that relate to treatment of diseases using extracellular vesicles derived from bacteria belonging to the genus *Bacillus* or lactic acid bacteria are disclosed (KR 10-1862507 and KR 10-1726488), but to date, the fact that bacteria belonging to the genus *Proteus* extracellularly secrete vesicles has not been reported, and particularly there are no reports of the use of bacteria belonging to the genus *Proteus* in the diagnosis and treatment of diseases such as cancer, cardiovascular diseases, metabolic diseases, neuropsychiatric diseases, allergic-respiratory diseases, inflammatory bowel diseases, and the like.

Therefore, it was confirmed in the present invention that the amount of vesicles derived from bacteria belonging to the genus *Proteus* was significantly reduced in clinical samples of patients with cancer, cardiovascular diseases, metabolic diseases, neuropsychiatric diseases, allergic-respiratory diseases, and inflammatory bowel diseases, as compared to that of normal people, and thus the diseases could be diagnosed. In addition, it was confirmed that vesicles isolated from culture broths of bacteria belonging to the genus *Proteus* could be used as a composition for preventing or treating cancer, cardiovascular diseases, metabolic diseases, neuropsychiatric diseases, allergic-respiratory diseases, and inflammatory bowel diseases.

DESCRIPTION OF EMBODIMENTS

Technical Problem

As a result of having conducted intensive studies to address the above-described conventional problems, the inventors of the present invention confirmed through metagenomic analysis that the amount of vesicles derived from bacteria belonging to the genus *Proteus* was significantly reduced, as compared to that of normal people, in samples derived from patients with cancers such as stomach cancer, colorectal cancer, liver cancer, bile duct cancer, pancreatic cancer, lung cancer, breast cancer, ovarian cancer, bladder cancer, prostate cancer, lymphoma, a brain tumor, and the like; cardiovascular diseases such as myocardial infarction, cardiomyopathy, atrial fibrillation, variant angina, a stroke, and the like; metabolic diseases such as diabetes, and the like; neuropsychiatric diseases such as Parkinson's disease, depression, and the like; allergic-respiratory diseases such as atopic dermatitis, asthma, chronic obstructive pulmonary disease (COPD), and the like; or inflammatory bowel diseases such as irritable bowel syndrome, inflammatory enteritis, and the like.

It was also confirmed that, when vesicles were isolated from *Proteus mirabilis*, which is a bacterium belonging to the genus *Proteus*, and inflammatory cells were treated with the vesicles, the secretion of TNF-α due to pathogenic vesicles was significantly inhibited, and as a result of evaluating anticancer efficacy, when mouse cancer disease models were orally administered vesicles derived from *Proteus mirabilis*, the onset of cancer was significantly inhibited, and thus the present invention was completed based on these findings.

Therefore, an object of the present invention is to provide a method of providing information for the diagnosis of one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression.

Another object of the present invention is to provide a composition for preventing, treating, and/or alleviating one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression, the composition including vesicles derived from bacteria belonging to the genus *Proteus* as an active ingredient.

However, technical problems to be achieved by the present invention are not limited to the above-described technical problems, and other unmentioned technical problems will become apparent from the following description to those of ordinary skill in the art.

Technical Solution

To achieve the above-described objects of the present invention, the present invention provides a method of providing information for the diagnosis of one or more diseases selected from the group consisting of cancer, a cardiovascular disease, a metabolic disease, a neuropsychiatric disease, an allergic-respiratory disease, and an inflammatory bowel disease, the method including the following processes:

(a) extracting DNA from vesicles isolated from normal people-derived samples and subject-derived samples;

(b) performing polymerase chain reaction (PCR) on the extracted DNA by using a pair of primers prepared based on a gene sequence present in 16S rDNA to obtain respective PCR products; and (c) determining a case, in which the amount of vesicles derived from bacteria belonging to the genus *Proteus* is lower than that of normal people, as one or more diseases selected from the group consisting of cancer, a cardiovascular disease, a metabolic disease, a neuropsychiatric disease, an allergic-respiratory disease, and an inflammatory bowel disease, through quantitative analysis of the PCR products.

The present invention also provides a method of diagnosing one or more diseases selected from the group consisting of cancer, a cardiovascular disease, a metabolic disease, a neuropsychiatric disease, an allergic-respiratory disease, and an inflammatory bowel disease, the method including the following processes:

(a) extracting DNA from vesicles isolated from normal people-derived samples and subject-derived samples;

(b) performing PCR on the extracted DNA by using a pair of primers prepared based on a gene sequence present in 16S rDNA to obtain respective PCR products; and (c) determining a case, in which the amount of vesicles derived from bacteria belonging to the genus *Proteus* is lower than that of normal people, as one or more diseases selected from the group consisting of cancer, a cardiovascular disease, a metabolic disease, a neuropsychiatric disease, an allergic-respiratory disease, and an inflammatory bowel disease, through quantitative analysis of the PCR products.

In another embodiment of the present invention, in process (a), the samples may be blood, urine, or stool.

The present invention also provides a pharmaceutical composition for preventing or treating one or more diseases selected from the group consisting of cancer, a cardiovascular disease, a metabolic disease, a neuropsychiatric disease, an allergic-respiratory disease, and an inflammatory bowel disease, the pharmaceutical composition including vesicles derived from bacteria belonging to the genus *Proteus* as an active ingredient.

The present invention also provides an inhalant composition for preventing or treating one or more diseases selected from the group consisting of cancer, a cardiovascular disease, a metabolic disease, a neuropsychiatric disease, an allergic-respiratory disease, and an inflammatory bowel disease, the inhalant composition including vesicles derived from bacteria belonging to the genus *Proteus* as an active ingredient.

The present invention also provides a composition for preventing or alleviating one or more diseases selected from the group consisting of cancer, a cardiovascular disease, a metabolic disease, a neuropsychiatric disease, an allergic-respiratory disease, and an inflammatory bowel disease, the composition including vesicles derived from bacteria belonging to the genus *Proteus* as an active ingredient.

In one embodiment of the present invention, the composition for preventing or alleviating the above-described diseases may be a food composition or a cosmetic composition.

In another embodiment of the present invention, the food composition may be a health functional food composition.

The present invention also provides a method of preventing or treating one or more diseases selected from the group consisting of cancer, a cardiovascular disease, a metabolic disease, a neuropsychiatric disease, an allergic-respiratory disease, and an inflammatory bowel disease, the method including administering, to an individual, a pharmaceutical composition including vesicles derived from bacteria belonging to the genus *Proteus* as an active ingredient.

The present invention also provides a use of vesicles derived from bacteria belonging to the genus *Proteus* for preventing or treating one or more diseases selected from the group consisting of cancer, a cardiovascular disease, a metabolic disease, a neuropsychiatric disease, an allergic-respiratory disease, and an inflammatory bowel disease.

In one embodiment of the present invention, the cancer may be stomach cancer, colorectal cancer, liver cancer, bile duct cancer, pancreatic cancer, lung cancer, breast cancer, ovarian cancer, bladder cancer, prostate cancer, lymphoma, or a brain tumor.

In another embodiment of the present invention, the cardiovascular disease may be myocardial infarction, cardiomyopathy, atrial fibrillation, variant angina, or a stroke.

In another embodiment of the present invention, the metabolic disease may be diabetes.

In another embodiment of the present invention, the neuropsychiatric disease may be Parkinson's disease or depression.

In another embodiment of the present invention, the allergic-respiratory disease may be atopic dermatitis, asthma, or chronic obstructive pulmonary disease.

In another embodiment of the present invention, the inflammatory bowel disease may be irritable bowel syndrome or inflammatory enteritis.

In another embodiment of the present invention, the vesicles may have an average diameter of 10 nm to 200 nm.

In another embodiment of the present invention, the vesicles may be naturally or artificially secreted from bacteria belonging to the genus *Proteus*.

In another embodiment of the present invention, the vesicles derived from bacteria belonging to the genus *Proteus* may be secreted from *Proteus mirabilis*.

Advantageous Effects of Invention

The inventors of the present invention confirmed that although intestinal bacteria would not be absorbed into the body, bacteria-derived vesicles were absorbed into the body through epithelial cells and distributed systemically, and excreted outside the body through the kidneys, the liver, and the lungs, and confirmed through metagenomic analysis of bacteria-derived vesicles present in blood, urine, stool, or the like of patients that vesicles derived from bacteria belonging to the genus *Proteus*, which are present in blood, urine, or stool of patients with cancers such as stomach cancer, colorectal cancer, liver cancer, bile duct cancer, pancreatic cancer, lung cancer, breast cancer, ovarian cancer, bladder cancer, prostate cancer, lymphoma, a brain tumor, and the like; cardiovascular diseases such as myocardial infarction, cardiomyopathy, atrial fibrillation, variant angina, a stroke, and the like; metabolic diseases such as diabetes, and the like; neuropsychiatric diseases such as Parkinson's disease, depression, and the like; allergic-respiratory diseases such as atopic dermatitis, asthma, chronic obstructive pulmonary disease (COPD), and the like; inflammatory bowel diseases such as irritable bowel syndrome, inflammatory enteritis, and the like, was significantly reduced as compared to that of normal people. In addition, it was observed that, when *Proteus mirabilis*, which is one species of bacteria belonging to the genus *Proteus*, was cultured in vitro, and vesicles were isolated therefrom and administered to in vitro inflammatory cells, the secretion of inflammatory mediators due to pathogenic vesicles was significantly inhibited, and when the vesicles were orally administered to mice, the onset of cancer was significantly inhibited, and thus it is anticipated that the vesicles derived from bacteria belonging to the genus *Proteus* according to the present invention can be usefully used in a method of diagnosing cancers such as stomach cancer, colorectal cancer, liver cancer, bile duct cancer, pancreatic cancer, lung cancer, breast cancer, ovarian cancer, bladder cancer, prostate cancer, lymphoma, a brain tumor, and the like; cardiovascular diseases such as myocardial infarction, cardiomyopathy, atrial fibrillation, variant angina, a stroke, and the like; metabolic diseases such as diabetes, and the like; neuropsychiatric diseases such as Parkinson's disease, depression, and the like; allergic-respiratory diseases such as atopic dermatitis, asthma, chronic obstructive pulmonary disease, and the like; inflammatory bowel diseases such as irritable bowel syndrome, inflammatory enteritis, and the like, and a composition for prevention, treatment, and/or alleviation, such as a food, an inhalant, a cosmetic, a drug, or the like.

BRIEF DESCRIPTION OF DRAWINGS

FIG. 1A illustrates images showing distribution patterns of bacteria and vesicles according to time after bacteria and bacteria-derived vesicles (EV) were orally administered to mice.

FIG. 1B illustrates images obtained as a result of evaluating in vivo distribution patterns of bacteria and vesicles in blood, the kidneys, the liver, and various organs which were extracted at 12 hours after bacteria and bacteria-derived vesicles (EV) were orally administered to mice.

FIG. 2 illustrates results of comparing distribution patterns of vesicles derived from bacteria belonging to the genus *Proteus* after metagenomic analysis was performed on bacteria-derived vesicles present in stool, blood, and urine samples of patients with stomach cancer and normal people.

FIG. 3 illustrates results of comparing distribution patterns of vesicles derived from bacteria belonging to the genus *Proteus* after metagenomic analysis was performed on bacteria-derived vesicles present in stool and urine samples of patients with colorectal cancer and normal people.

FIG. 4 illustrates results of comparing distribution patterns of vesicles derived from bacteria belonging to the genus *Proteus* after metagenomic analysis was performed on bacteria-derived vesicles present in blood samples of patients with liver cancer, bile duct cancer, or pancreatic cancer, and normal people.

FIG. 5 illustrates results of comparing distribution patterns of vesicles derived from bacteria belonging to the genus *Proteus* after metagenomic analysis was performed on bacteria-derived vesicles present in blood samples of patients with lung cancer and normal people.

FIG. 6 illustrates results of comparing distribution patterns of vesicles derived from bacteria belonging to the genus *Proteus* after metagenomic analysis was performed on bacteria-derived vesicles present in urine samples of patients with breast cancer or ovarian cancer, and normal people.

FIG. 7 illustrates results of comparing distribution patterns of vesicles derived from bacteria belonging to the genus *Proteus* after metagenomic analysis was performed on bacteria-derived vesicles present in blood and urine samples of patients with bladder cancer and normal people.

FIG. 8 illustrates results of comparing distribution patterns of vesicles derived from bacteria belonging to the genus *Proteus* after metagenomic analysis was performed on bacteria-derived vesicles present in urine samples of patients with prostate cancer and normal people.

FIG. 9 illustrates results of comparing distribution patterns of vesicles derived from bacteria belonging to the genus *Proteus* after metagenomic analysis was performed on bacteria-derived vesicles present in blood samples of patients with lymphoma or a brain tumor and normal people.

FIG. 10 illustrates results of comparing distribution patterns of vesicles derived from bacteria belonging to the genus *Proteus* after metagenomic analysis was performed on bacteria-derived vesicles present in blood samples of patients with diabetes and normal people.

FIG. 11 illustrates results of comparing distribution patterns of vesicles derived from bacteria belonging to the genus *Proteus* after metagenomic analysis was performed on bacteria-derived vesicles present in blood samples of patients with myocardial infarction, cardiomyopathy, atrial fibrillation, or variant angina and normal people.

FIG. 12 illustrates results of comparing distribution patterns of vesicles derived from bacteria belonging to the genus *Proteus* after metagenomic analysis was performed on bacteria-derived vesicles present in blood samples of patients with a stroke and normal people.

FIG. 13 illustrates results of comparing distribution patterns of vesicles derived from bacteria belonging to the genus *Proteus* after metagenomic analysis was performed on bacteria-derived vesicles present in urine samples of patients with Parkinson's disease or depression and normal people.

FIG. 14 illustrates results of comparing distribution patterns of vesicles derived from bacteria belonging to the genus *Proteus* after metagenomic analysis was performed on bacteria-derived vesicles present in blood samples of patients with atopic dermatitis and normal people.

FIG. 15 illustrates results of comparing distribution patterns of vesicles derived from bacteria belonging to the genus *Proteus* after metagenomic analysis was performed on bacteria-derived vesicles present in blood samples of patients with asthma or chronic obstructive pulmonary disease (COPD) and normal people.

FIG. 16 illustrates results of comparing distribution patterns of vesicles derived from bacteria belonging to the genus *Proteus* after metagenomic analysis was performed on bacteria-derived vesicles present in stool samples of patients with irritable bowel syndrome, inflammatory enteritis, and normal people.

FIG. 17A illustrates a microscope image showing observation results of vesicles isolated from a culture broth obtained after *Proteus mirabilis* was cultured in vitro.

FIG. 17B illustrates results of measuring the size of vesicles isolated from a *Proteus mirabilis* culture broth, by dynamic light scattering.

FIGS. 18A and 18B illustrate results of evaluating an effect of *E. coli* vesicles (*E. coli* EV) on the secretion of IL-6 (FIG. 18A) and TNF-α (FIG. 18B), which are inflammatory mediators, in the case of pretreatment with vesicles derived from bacteria belonging to the genus *Proteus* prior to treatment with the *E. coli* vesicles, which are pathogenic vesicles, to evaluate an anti-inflammatory effect of *Proteus mirabilis*-derived vesicles.

FIG. 19 illustrate results of evaluating an effect of *E. coli* vesicles (*E. coli* EV) on the secretion of TNF-α, in the case of pretreatment with *Proteus mirabilis* (PMR)-derived vesicles isolated from people prior to treatment with *E. coli* vesicles, which are pathogenic vesicles, to compare effects of vesicles derived from various strains with the anti-inflammatory effect of *Proteus mirabilis*-derived vesicles (NC: negative control; PC: positive control; *L. plantarum*: *Lactobacillus plantarum*).

FIG. 20 illustrate results of evaluating an effect of *E. coli* vesicles on the secretion of TNF-α, in the case of pretreatment with heat-treated or acid-treated *Proteus mirabilis* (PMR)-derived vesicles before treatment with the *E. coli* vesicles (*E. coli* EV), which are pathogenic vesicles, to evaluate an effect of heat treatment or acid treatment on the anti-inflammatory effect of *Proteus mirabilis*-derived vesicles (NC: negative control; PC: positive control; *L. plantarum*: *Lactobacillus plantarum*).

FIG. 21A illustrates a protocol by which *Proteus mirabilis*-derived vesicles were administered to mice to evaluate the anticancer efficacy of the *Proteus mirabilis*-derived vesicles.

FIG. 21B illustrates results of evaluating an effect of *Proteus mirabilis*-derived vesicles on tumorigenesis due to cancer cells when orally administered to mice.

BEST MODE

The present invention relates to vesicles derived from bacteria belonging to the genus *Proteus* and a use thereof.

The inventors of the present invention confirmed through metagenomic analysis that the amount of vesicles derived from bacteria belonging to the genus *Proteus* was significantly reduced, as compared to that of normal people, in samples derived from patients with cancers such as stomach cancer, colorectal cancer, liver cancer, bile duct cancer, pancreatic cancer, lung cancer, breast cancer, ovarian cancer, bladder cancer, prostate cancer, lymphoma, a brain tumor, and the like; cardiovascular diseases such as myocardial infarction, cardiomyopathy, variant angina, atrial fibrillation, a stroke, and the like; metabolic diseases such as diabetes, and the like; neuropsychiatric diseases such as Parkinson's disease, depression, and the like; allergic-respiratory diseases such as atopic dermatitis, asthma, chronic obstructive pulmonary disease, and the like; or inflammatory bowel diseases such as irritable bowel syndrome, inflammatory enteritis, and the like, and thus completed the present invention based on these findings.

Therefore, the present invention provides a method of providing information for the diagnosis of one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression, the method including the following processes:

(a) extracting DNA from vesicles isolated from normal people-derived samples and subject-derived samples;

(b) performing PCR on the extracted DNA by using a pair of primers prepared based on a gene sequence present in 16S rDNA to obtain respective PCR products; and (c) determining a case, in which the amount of vesicles derived from bacteria belonging to the genus *Proteus* is lower than that of normal people, as one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression, through quantitative analysis of the PCR products.

The term "diagnosis" as used herein means, in a broad sense, determining conditions of disease of a patient in all aspects. Content of the determination includes disease name, the cause of a disease, the type of disease, the severity of disease, detailed aspects of syndrome, the presence or absence of complications, prognosis, and the like. In the present invention, diagnosis means determining the presence or absence of the onset of cancer, a cardiovascular disease, a metabolic disease, a neuropsychiatric disease, an allergic-respiratory disease, or an inflammatory bowel disease, the severity of disease, and the like.

The term "cancer," which is a diagnostic target disease of the present invention, means malignant tumors that grow rapidly while infiltrating into the surrounding tissues and diffuse or transit to each part of the body, and thus are life-threatening. Cells, which are the smallest unit of the body, normally divide and grow by the regulatory function of cells themselves, and when the lifespan of cells end or cells get damaged, they themselves die and thus maintain a balance in an overall number of cells. However, when cells have a problem with such a regulatory function thereof, due to various causes, abnormal cells, which would normally die, excessively proliferate, and infiltrate into the surrounding tissues and organs to thereby form a mass, resulting in destruction or modification of existing structures. In the present invention, the cancer may be preferably stomach cancer, colorectal cancer, liver cancer, bile duct cancer, pancreatic cancer, lung cancer, breast cancer, ovarian cancer, bladder cancer, prostate cancer, lymphoma, a brain tumor, but the present invention is not limited thereto.

The term "cardiovascular disease" as used herein means the onset of a disease in the cardiovascular system of a mammal, and examples thereof include heart diseases such as myocardial infarction, cardiomyopathy, angina, arrhythmia, and the like; vasculitis; cerebrovascular diseases such as dementia, a stroke, and the like; and the like. In the present invention, the cardiovascular disease preferably includes, but is not limited to, myocardial infarction, cardiomyopathy, variant angina, atrial fibrillation, or a stroke.

The term "metabolic disease" as used herein refers to a disease in which complications occur in various organs due to metabolic disorders in the body of a mammal, and examples thereof include metabolic disorders such as hyperlipidemia, diabetes, and the like, complications thereof, and the like. In the present invention, the metabolic disease preferably includes, but is not limited to, diabetes.

The term "neuropsychiatric disease" as used herein refers to a disease occurring in the nervous system and brain of a mammal, and examples thereof include brain diseases such as Parkinson's disease, dementia, and the like; mental diseases such as depression, obsessive-compulsive disorder, schizophrenia, and the like; and the like. In the present invention, the neuropsychiatric disease preferably includes, but is not limited to, Parkinson's disease and depression.

The term "allergic disease" as used herein refers to a disease caused by allergic mechanisms in mammals, and examples thereof include skin diseases such as atopic dermatitis, respiratory diseases such as allergic rhinitis and asthma, and the like. In the present invention, the allergic disease preferably includes, but is not limited to, atopic dermatitis and asthma.

The term "respiratory disease" as used herein refers to a disease occurring in the respiratory system of a mammal, and examples thereof include rhinitis, asthma, chronic obstructive pulmonary disease, and the like. In the present invention, the respiratory disease preferably includes, but is not limited to, asthma and chronic obstructive pulmonary disease.

The term "inflammatory bowel disease" as used herein refers to unidentified chronic inflammation occurring in the intestines, and in a broad sense, may include all inflammatory diseases occurring in the intestines, such as infectious enteritis and ischemic bowel disease such as bacterial, viral, amoebic, or tuberculous enteritis, and the like; radiation enteritis; and the like. In the present invention, the inflammatory bowel disease preferably includes, but is not limited to, irritable bowel syndrome and inflammatory enteritis.

The term "nanovesicles" or "vesicles" as used herein refers to structures consisting of nano-sized membranes secreted by various bacteria. Gram-negative bacteria-derived vesicles, or outer membrane vesicles (OMVs) contain lipopolysaccharides, toxic proteins, bacterial DNA and RNA, and various metabolites, and gram-positive bacteria-derived vesicles also contain peptidoglycan and lipoteichoic acid, which are cell wall components of bacteria, in addition to proteins and nucleic acids. In the present invention, nanovesicles or vesicles are naturally secreted or artificially produced in bacteria belonging to the genus *Proteus*, and have an average diameter of 10 nm to 200 nm.

The vesicles may be isolated from a culture broth containing bacteria belonging to the genus *Proteus* by using one or more methods selected from centrifugation, ultracentrifugation, extrusion, ultrasonic degradation, cell lysis, homogenization, freezing-thawing, electroporation, mechanical degradation, chemical treatment, filtration using a filter, gel filtration chromatography, free-flow electrophoresis, and capillary electrophoresis. In addition, the isolation methods may further include washing for the removal of impurities, concentration of obtained vesicles, and the like.

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at one time using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as an existing species functionally interact with each other to form a complete species. Technically, it is the subject of techniques that analyze all DNAs and RNAs regardless of species using rapid sequencing to identify all species in one environment and verify interactions and metabolism.

In the present invention, the samples may be, but is not limited to, blood, urine, or stool.

According to another embodiment of the present invention, there is provided a pharmaceutical composition for preventing or treating one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression, the pharmaceutical composition including vesicles derived from bacteria belonging to the genus *Proteus* as an active ingredient.

According to another embodiment of the present invention, there is provided an inhalant composition for preventing or treating one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression, the inhalant composition including vesicles derived from bacteria belonging to the genus *Proteus* as an active ingredient.

According to another embodiment of the present invention, there is provided a composition for preventing or alleviating one or more diseases selected from the group consisting of stomach cancer, colorectal cancer, liver cancer, bile duct cancer, pancreatic cancer, lung cancer, breast cancer, ovarian cancer, bladder cancer, prostate cancer, lymphoma, a brain tumor, chronic obstructive pulmonary disease, atopic dermatitis, irritable bowel syndrome, inflammatory enteritis, asthma, myocardial infarction, cardiomyopathy, variant angina, atrial fibrillation, a stroke, diabetes, Parkinson's disease, and depression, the composition including vesicles derived from bacteria belonging to the genus *Proteus* as an active ingredient. The composition includes a food composition and a cosmetic composition.

The term "prevention" as used herein means all actions that inhibit cancer, a cardiovascular disease, a metabolic disease, a neuropsychiatric disease, an allergic-respiratory disease, and an inflammatory bowel disease or delay the onset thereof via administration of the pharmaceutical composition according to the present invention.

The term "treatment" as used herein means all actions that alleviate or beneficially change symptoms due to cancer, a cardiovascular disease, a metabolic disease, a neuropsychiatric disease, an allergic-respiratory disease, and an inflammatory bowel disease via administration of the pharmaceutical composition according to the present invention.

The term "alleviation" as used herein means all actions that decrease at least the degree of parameters related to conditions being treated, e.g., symptoms.

In one embodiment of the present invention, it was confirmed that, as a result of evaluating in vivo absorption, distribution and excretion patterns of bacteria and bacteria-derived vesicles after being orally administered to mice, the bacteria were not absorbed through the intestinal mucosa, while the vesicles were absorbed within 5 minutes after administration and distributed systemically, and excreted through the kidneys, the liver, and the like (see Example 1).

In another embodiment of the present invention, bacterial metagenomic analysis was performed using vesicles isolated from blood, urine, or stool samples of patients with stomach cancer, colorectal cancer, liver cancer, bile duct cancer, pancreatic cancer, lung cancer, breast cancer, ovarian cancer, bladder cancer, prostate cancer, lymphoma, or a brain tumor, and a normal control having age matched with that of the patients. As a result, it was confirmed that vesicles derived from bacteria belonging to the genus *Proteus* was significantly reduced in samples of patients with stomach cancer, colorectal cancer, liver cancer, bile duct cancer, pancreatic cancer, lung cancer, breast cancer, ovarian cancer, bladder cancer, prostate cancer, lymphoma, or a brain tumor, as compared to that of samples of normal people (see Example 3).

In another embodiment of the present invention, bacterial metagenomic analysis was performed using vesicles isolated from samples of patients with diabetes, myocardial infarction, cardiomyopathy, atrial fibrillation, variant angina, or a stroke, and samples of normal people having age matched with that of the patients. As a result, it was confirmed that vesicles derived from bacteria belonging to the genus *Proteus* was significantly reduced in the samples of patients with diabetes, myocardial infarction, cardiomyopathy, variant angina, atrial fibrillation, or a stroke, as compared to that of the samples of normal people (see Example 4).

In another embodiment of the present invention, bacterial metagenomic analysis was performed using vesicles isolated from samples of patients with Parkinson's disease or depression, and samples of normal people having age matched with that of the patients. As a result, it was confirmed that vesicles derived from bacteria belonging to the genus *Proteus* was significantly reduced in the samples of patients with Parkinson's disease or depression, as compared to the samples of normal people (see Example 5).

In another embodiment of the present invention, bacterial metagenomic analysis was performed using vesicles isolated from samples of patients with atopic dermatitis, asthma, or chronic obstructive pulmonary disease, and samples of normal people having age and gender matched with those of the patients. As a result, it was confirmed that vesicles derived from bacteria belonging to the genus *Proteus* was significantly reduced in the samples of patients with atopic dermatitis, asthma, or chronic obstructive pulmonary disease, as compared to that of the samples of normal people (see Example 6).

In another embodiment of the present invention, bacterial metagenomic analysis was performed using vesicles isolated from samples of patients with irritable bowel syndrome or inflammatory enteritis, and normal people having age matched with that of the patients. As a result, it was confirmed that vesicles derived from bacteria belonging to the genus *Proteus* was significantly reduced in the samples of patients with irritable bowel syndrome or inflammatory enteritis, as compared to that of the samples of normal people (see Example 7).

In another embodiment of the present invention, as a result of further having conducted studies to analyze the characteristics of vesicles derived from bacteria belonging to the genus *Proteus*, i.e., *Proteus mirabilis*, based on the results of the above-described examples, it was confirmed that the vesicles had an average diameter of less than 200 nm, preferably 41.40±5.03 nm, and were spherical (see Example 8).

In another embodiment of the present invention, as a result of evaluating the secretion of an inflammatory mediator after *Proteus mirabilis* stains isolated from people were cultured, and then macrophages were treated with *Proteus mirabilis*-derived vesicles at various concentrations and treated with *E. coli*-derived vesicles, which are causative factors of an inflammatory disease, a metabolic disease, and cancer, to examine whether vesicles secreted from culture broths of the *Proteus mirabilis* strains have an anti-inflammatory effect, it was confirmed that the secretion of TNF-α due to *E. coli*-derived vesicles was efficiently inhibited in all the cases of *Proteus mirabilis*-derived vesicles regardless of the origin of *Proteus mirabilis* (see Example 9).

In another embodiment of the present invention, to evaluate whether an active material of *Proteus mirabilis*, which exhibits an anti-inflammatory effect, is a low-molecular-weight compound or protein included in vesicles, *Proteus mirabilis*-derived vesicles were heat-treated or acid-treated. Subsequently, as a result of evaluating the effect of heat-treated or acid-treated vesicles on the secretion of TNF-α after being administered to macrophages prior to treatment with *E. coli*-derived vesicles, it was confirmed that the secretion of TNF-α due to *E. coli*-derived vesicles was efficiently inhibited in both cases of the heat-treated or acid-treated *Proteus mirabilis*-derived vesicles (see Example 10).

In another embodiment of the present invention, to evaluate whether vesicles secreted from culture broths of *Proteus mirabilis* strains exhibit an anticancer therapeutic effect, cancer disease models were prepared by subcutaneously injecting a cancer cell line, and as a result of measuring the size of cancer tissue for 20 days after the *Proteus mirabilis*-derived vesicles were orally administered to mice from 4 days before treatment, it was confirmed that the size of cancer tissue was significantly reduced in the case in which the vesicles were administered, as compared to that of a control (see Example 11).

The pharmaceutical composition according to the present invention includes vesicles derived from bacteria belonging to the genus *Proteus* as an active ingredient, and may include a pharmaceutically acceptable carrier. The pharmaceutically acceptable carrier includes carriers commonly used for formulation, e.g., saline, sterilized water, Ringer's solution, buffered saline, cyclodextrin, a dextrose solution, a maltodextrin solution, glycerol, ethanol, liposomes, and the like, but the present invention is not limited thereto, and if needed, may further include other general additives such as antioxidants, buffer solutions, and the like. In addition, preparations for injection, such as aqueous solutions, suspensions, emulsions, and the like, pills, capsules, granules, or tablets may be formulated by additionally adding a diluent, a dispersant, a surfactant, a binder, a lubricant, or the like. With regards to suitable pharmaceutically acceptable carriers and formulations, preparations may be preferably formulated according to each ingredient by using a method disclosed in the Remington's reference. Preparations of the pharmaceutical composition of the present invention are not particularly limited, but the pharmaceutical composition may be formulated into the form of injections, inhalants, external preparations for skin, oral ingestions, or the like.

The pharmaceutical composition of the present invention may be administered orally or parenterally (e.g., intravenous administration, subcutaneous administration, intradermal administration, intranasal administration, and intra-airway administration) according to a target method, and a suitable dose thereof may vary depending on the condition and body weight of a patient, the severity of disease, the type of drug, administration routes, and administration time, and may be appropriately selected by those of ordinary skill in the art.

The composition according to the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including the type of disease of a patient, the severity of disease, drug activity, sensitivity to a drug, administration time, administration routes, excretion rate, treatment period, and simultaneously used drugs, and other factors well known in the medical field. The composition according to the present invention may be administered as an individual therapeutic agent or in combination with other therapeutic agents, may be administered consecutively or simultaneously with existing therapeutic agents, and may be administered in a single dose or multiple doses. It is important to administer the composition in the minimum amount that enables achievement of the maximum effects without side effects in consideration of all the above-described factors, and this may be easily determined by those of ordinary skill in the art.

In particular, an effective amount of the composition according to the present invention may vary according to the age, gender, and body weight of a patient. Generally, the composition may be administered in an amount of 0.001 mg to 150 mg, preferably, 0.01 mg to 100 mg, per body weight (1 kg) daily or every other day, or may be administered once or three times a day. However, the dosage may be increased or decreased according to administration routes, the severity of obesity, gender, body weight, age, and the like, and thus the dosage is not intended to limit the scope of the present invention in any way.

In a food composition of the present invention, the active ingredient may be added as is or used in combination with other foods or food ingredients, and it may be appropriately used according to a general method. A mixing amount of the active ingredient may be appropriately determined according to the purpose of use (for prevention or alleviation). Generally, when preparing foods or beverages, the composition of the present invention is added in an amount of 15 wt % or less, preferably 10 wt % or less, with respect to the amount of raw materials. However, in the case of long-term administration for health and hygienic purposes or for health control, an amount less than the above-described range may be used.

In addition to the active ingredient included as an essential ingredient in the food composition of the present invention at the indicated ratio, other ingredients of the food composition are not particularly limited, and the food composition may include various flavoring agents, natural carbohydrates, or the like as additional ingredients, like general beverages. Examples of the above-described natural carbohydrates include general sugars, for example, monosaccharides such as glucose, fructose, and the like; disaccharides such as maltose, sucrose, and the like; and polysaccharides such as dextrin, cyclodextrin, and the like, and sugar alcohols such as xylitol, sorbitol, erythritol, and the like. Examples of sweeteners other than the above-described carbohydrates may include natural sweeteners such as thaumatin and stevia extracts (e.g., rebaudioside A, glycyrrhizin, and the like), and synthetic sweeteners such as saccharin, aspartame, and the like. The proportion of the natural carbohydrate may be appropriately determined by those of ordinary skill in the art.

In addition, the food composition of the present invention may include various nutritional supplements, vitamins, minerals (electrolytes), flavors such as synthetic flavors, natural flavors, and the like, colorants and enhancers (cheese, chocolates, and the like), pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. These ingredients may be used alone or a combination thereof may be used. The proportion of these additives may also be appropriately selected by those of ordinary skill in the art.

A cosmetic composition of the present invention may include not only vesicles derived from bacteria belonging to the genus *Proteus*, but also ingredients commonly used in cosmetic compositions, and may include, for example, general adjuvants such as an antioxidant, a stabilizer, a solubilizing agent, vitamins, pigments, and dyes, and a carrier.

In addition, the composition of the present invention may further include, in addition to the vesicles derived from bacteria belonging to the genus *Proteus*, an organic UV blocking agent that has long been used within a range that does not adversely affect a skin protective effect by reaction with vesicles derived from bacteria belonging to the genus *Proteus*. The organic UV blocking agent may be one or more selected from the group consisting of glyceryl PABA, drometrizole trisiloxane, drometrizole, digalloyl trioleate, disodium phenyl dibenzimidazole tetrasulfonate, diethyl hexyl butamidotriazone, diethyl amino hydroxyl benzoyl hexyl benzoate, DEA-methoxycinnamate, a mixture of lawsone and dihydroxyacetone, methylenebis-benzotriazolyltetramethylbutylphenol, 4-methylbenzylidene camphor, menthyl anthranilate, benzophenone-3 (oxybenzone), benzophenone-4, benzophenone-8(dioxybenzone), butyl-methoxydibenzoylmethane, bisethylhexyloxyphenol-methoxyphenyltriazine, cinoxate, ethyldihydroxypropyl PABA, octocrylene, ethylhexyldimethyl PABA, ethylhexyl-methoxycinnamate, ethylhexyl salicylate, ethylhexyl triazone, isoamyl-p-methoxycinnamate, polysilicon-15(dimethicodiethylbenzal malonate), terephthalylidene dicamphor sulfonic acid and salts thereof, TEA-salicylate, and aminobenzoic acid (PABA).

Examples of products to which the cosmetic composition of the present invention may be added include cosmetics such as astringents, skin softeners, nourishing toners, various creams, essences, packs, foundations, and the like, cleansing, face cleansers, soaps, treatments, beauty liquids, and the like. Particular preparations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a press powder, a loose powder, an eye shadow, and the like.

According to an exemplary embodiment of the present invention, the amount of the vesicles derived from bacteria belonging to the genus *Proteus* of the present invention ranges from 0.00001 wt % to 30 wt %, preferably 0.5 wt % to 20 wt %, and more preferably 1.0 wt % to 10 wt %, with respect to a total weight of the composition.

In the inhalant composition of the present invention, the active ingredient may be directly added to an inhalant or may be used in combination with other ingredients, and may be appropriately used according to a general method. A mixing amount of the active ingredient may be appropriately determined according to the purpose of use (for prevention or treatment).

Hereinafter, exemplary embodiments will be described to aid in understanding of the present invention. However, the following examples are provided only to facilitate the understanding of the present invention and are not intended to limit the scope of the present invention.

MODE OF INVENTION

EXAMPLES

Example 1

Analysis of In Vivo Absorption, Distribution, and Excretion Patterns of Intestinal Bacteria and Bacteria-Derived Vesicles Experiments were conducted using the following method to evaluate whether intestinal bacteria and bacteria-derived vesicles were systemically absorbed through the gastrointestinal tract. Intestinal bacteria and intestinal bacteria-derived vesicles, which were labeled with fluorescence, were administered to the gastrointestinal tract of mice at a dose of 50 μg, and fluorescence was measured after 0 minute, 5 minutes, 3 hours, 6 hours, and 12 hours.

As a result of observing the whole images of mice, as illustrated in FIG. 1A, while the bacteria were not systemically absorbed, the bacteria-derived vesicles were systemically absorbed at 5 minutes after administration, strong fluorescence was observed in the bladder at 3 hours after administration, thereby confirming that the vesicles were excreted into the urinary tract. In addition, it was confirmed that the vesicles were present in the body until 12 hours (see FIG. 1A).

To evaluate the infiltration patterns of intestinal bacteria and intestinal bacteria-derived vesicles into various organs after being systemically absorbed, 50 μg of bacteria and bacteria-derived vesicles that were labeled with fluorescence were administered using the above-described method, and then blood, the heart, the liver, the kidneys, the spleen, fat, and muscle were extracted 12 hours after administration.

As a result of observing fluorescence in the collected tissues, as illustrated in FIG. 1B, it was seen that the bacteria-derived vesicles were distributed in blood, the heart, the lungs, the liver, the kidneys, the spleen, fat, and muscle, while the bacteria were not absorbed (see FIG. 1B).

Example 2

Metagenomic Analysis of Bacteria-Derived Vesicles in Clinical Samples

First, clinical samples such as blood, urine, stool, and the like were centrifuged (3,500×g, 10 minutes, 4° C.) in a 10 ml tube to precipitate a floating material and only a supernatant was transferred into a new 10 ml tube. Bacteria and impurities were removed therefrom using a 0.22 μm filter, and then the resulting supernatant was transferred into centripreigugal filters (50 kD), centrifuged at 1,500×g and 4° C. for 15 minutes to remove a material having a size of less than 50 kD, and concentrated up to 10 ml. Bacteria and impurities were removed again therefrom using a 0.22 μm filter, and then subjected to ultrahigh speed centrifugation at 150,000×g and 4° C. for 3 hours using a Type 90 ti rotor to remove a supernatant, and the agglomerated pellet was dissolved with phosphate buffered saline (PBS).

100 μl of the vesicles isolated using the above-described method were boiled at 100° C. to release internal DNA out of the lipid, and then cooled on ice for 5 minutes. Then, to remove the remaining floating materials, the resultant samples were centrifuged at 10,000×g and 4° C. for 30 minutes to collect only a supernatant. The amount of DNA was then quantified using Nanodrop, and then PCR was performed on the extracted DNA using a pair of 16S rDNA primers shown in Table 1 below to confirm the presence or absence of bacteria-derived DNA, thereby confirming the presence of bacteria-derived genes in the extracted DNA.

TABLE 1

| Primer | | Sequence | SEQ ID NO. |
| --- | --- | --- | --- |
| 16S rDNA | 16S_V3_F | 5'-TCGTCGGCAGCGTCAGATGTGTATAA GAGACAGCCTACGGGNGGCWGCAG-3' | 1 |
| | 16S_V4_R | 5'-GTCTCGTGGGCTCGGAGATGTGTATAA GAGACAGGACTACHVGGGTATCTAATCC-3' | 2 |

The DNA extracted using the above method was amplified using the pair of 16S rDNA primers, and then sequenced (Illumina MiSeq sequencer), the results were output in the form of a Standard Flowgram Format (SFF) file and the SFF file was converted into a sequence file (.fasta) and a nucleotide quality score file by using GS FLX software (v2.9), and then a reliability estimation for reads was identified and a portion with a window (20 bps) average base call accuracy of less than 99% (Phred score<20) was removed. For operational taxonomy unit (OTU) analysis, clustering was performed according to sequence similarity using UCLUST and USEARCH, the genus, family, order, class, and phylum were clustered based on the sequence similarities of 94%, 90%, 85%, 80%, and 75%, respectively, levels of the phylum, class, order, family, and genus of respective OTUs were classified, and bacteria having a sequence similarity of 97% or more at the genus level were profiled using a BLASTN and GreenGenes 16S RNA sequence database (108,453 sequences) (QIIME).

Example 3

Metagenomic Analysis of Bacteria-Derived Vesicles in Clinical Samples of Patients with Cancer Genes were extracted from vesicles present in stool samples of 55 patients with stomach cancer and 99 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the stool samples of the patients with stomach cancer, as compared to that of the stool samples of the normal people (normal people vs patients with stomach cancer: 1.1% vs 0.05%, p<0.001) (see FIG. 2).

In addition, genes were extracted from vesicles present in blood samples of 67 patients with stomach cancer and 198 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with stomach cancer, as compared to that of the blood samples of the normal people (normal people vs patients with stomach cancer: 1.3% vs 0.2%, p=<0.001) (see FIG. 2).

In addition, genes were extracted from vesicles present in urine samples of 61 patients with stomach cancer and 120 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with stomach cancer, as compared to that of the urine samples of the normal people (normal people vs patients with stomach cancer: 1.8% vs 0.1%, p<0.0001) (see FIG. 2).

In addition, genes were extracted from vesicles present in stool samples of 38 patients with colorectal cancer and 55 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the stool samples of the patients with colorectal cancer, as compared to that of the stool samples of the normal people (normal people vs patients with colorectal cancer: 1.2% vs 0.05%, p<0.001) (see FIG. 3).

In addition, genes were extracted from vesicles present in urine samples of 38 patients with colorectal cancer and 38 normal people, who had gender and age matched with those of the patients, as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with colorectal cancer, as compared to that of the urine samples of the normal people (normal people vs patients with colorectal cancer: 1.3% vs 0.06%, p<0.001) (see FIG. 3).

In addition, genes were extracted from vesicles present in blood samples of 94 patients with liver cancer and 152 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with liver cancer, as compared to that of the blood samples of the normal people (normal people vs patients with liver cancer: 0.7% vs 0.01%, p<0.001) (see FIG. 4).

In addition, genes were extracted from vesicles present in blood samples of 84 patients with bile duct cancer and 132 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with bile duct cancer, as compared to that of the blood samples of the normal people (normal people vs patients with bile duct cancer: 0.7% vs 0.06%, p<0.001) (see FIG. 4).

In addition, genes were extracted from vesicles present in blood samples of 191 patients with pancreatic cancer and 291 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with pancreatic cancer, as compared to that of the blood samples of the normal people (normal people vs patients with pancreatic cancer: 0.7% vs 0.06%, p<0.001) (see FIG. 4).

In addition, genes were extracted from vesicles present in blood samples of 318 patients with lung cancer and 234 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with lung cancer, as compared to that of the blood samples of the normal people (normal people vs patients with lung cancer: 0.7% vs 0.1%, p<0.001) (see FIG. 5).

In addition, genes were extracted from vesicles present in urine samples of 127 patients with breast cancer and 220 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with breast cancer, as compared to that of the urine samples of the normal people (normal people vs patients with breast cancer: 1.4% vs 0.3%, p<0.001) (see FIG. 6).

In addition, genes were extracted from vesicles present in urine samples of 136 patients with ovarian cancer and 136 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with ovarian cancer, as compared to that of the urine samples of the normal people (normal people vs patients with ovarian cancer: 1.1% vs 0.1%, p<0.001) (see FIG. 6).

In addition, genes were extracted from vesicles present in blood samples of 96 patients with bladder cancer and 184 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with bladder cancer, as compared to that of the blood samples of the normal people (normal people vs patients with bladder cancer: 0.8% vs 0.1%, p<0.001) (see FIG. 7).

In addition, genes were extracted from vesicles present in urine samples of 95 patients with bladder cancer and 157 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with bladder cancer, as compared to that of the urine samples of the normal people (normal people vs patients with bladder cancer: 1.9% vs 0.1%, p<0.000001) (see FIG. 7).

In addition, genes were extracted from vesicles present in urine samples of 53 patients with prostate cancer and 159 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with prostate cancer, as compared to that of the urine samples of the normal people (normal people vs patients with prostate cancer: 1.1% vs 0.09%, p<0.000001) (see FIG. 8).

In addition, genes were extracted from vesicles present in blood samples of 93 patients with lymphoma and 109 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with lymphoma, as compared to that of the blood samples of the normal people (normal people vs patients with lymphoma: 0.09% vs 0.00%, p<0.001) (see FIG. 9).

In addition, genes were extracted from vesicles present in blood samples of 84 patients with a brain tumor and 92 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with a brain tumor, as compared to that of the blood samples of the normal people (normal people vs patients with a brain tumor: 0.09% vs 0.01%, p<0.01) (see FIG. 9).

Example 4

Metagenomic Analysis of Bacteria-Derived Vesicles in Clinical Samples of Patients with Diabetes and Cardiovascular Disease Genes were extracted from vesicles present in blood samples of 73 patients with diabetes and 146 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with diabetes, as compared to that of the blood samples of the normal people (normal people vs patients with diabetes: 0.4% vs 0.01%, p<0.01) (see FIG. 10).

In addition, genes were extracted from vesicles present in blood samples of 57 patients with myocardial infarction and 163 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with myocardial infarction, as compared to that of the blood samples of the normal people (normal people vs patients with myocardial infarction: 0.4% vs 0.07%, p<0.01) (see FIG. 11).

In addition, genes were extracted from vesicles present in blood samples of 72 patients with cardiomyopathy and 163 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with cardiomyopathy, as compared to that of the blood samples of the normal people (normal people vs patients with cardiomyopathy: 0.4% vs 0.08%, p<0.01) (see FIG. 11).

In addition, genes were extracted from vesicles present in blood samples of 69 patients with atrial fibrillation and 103 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with atrial fibrillation, as compared to that of the blood samples of the normal people (normal people vs patients with atrial fibrillation: 0.1% vs 0.01%, p<0.01) (see FIG. 11).

In addition, genes were extracted from vesicles present in blood samples of 32 patients with variant angina and 32 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with variant angina, as compared to that of the blood samples of the normal people (normal people vs patients with variant angina: 0.6% vs 0.1%, p<0.05) (see FIG. 11). In addition, genes were extracted from vesicles present in blood samples of 87 patients with a stroke and 92 normal people as a control, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with a stroke, as compared to that of the blood samples of the normal people (normal people vs patients with a stroke: 0.3% vs 0.00%, p<0.05) (see FIG. 12).

Example 5

Metagenomic Analysis of Bacteria-Derived Vesicles in Clinical Samples of Patients with Neuropsychiatric Disease Genes were extracted from vesicles present in urine samples of 39 patients with Parkinson's disease and 79 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with Parkinson's disease, as compared to that of the urine samples of the normal people (normal people vs patients with Parkinson's disease: 0.6% vs 0.02%, p<0.0001) (see FIG. 13).

In addition, genes were extracted from vesicles present in urine samples of 20 patients with depression and 20 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the urine samples of the patients with depression, as compared to that of the urine samples of the normal people (normal people vs patients with depression: 1.7% vs 0.06%, p<0.01) (see FIG. 13).

Example 6

Metagenomic Analysis of Bacteria-Derived Vesicles in Clinical Samples of Patients with Allergic or Respiratory Disease Genes were extracted from vesicles present in blood samples of 27 patients with atopic dermatitis and 138 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with atopic dermatitis, as compared to that of the blood samples of the normal people (normal people vs patients with atopic dermatitis: 2.0% vs 0.06%, p<0.00001) (see FIG. 14).

In addition, genes were extracted from vesicles present in blood samples of 291 patients with asthma, 207 patients with chronic obstructive pulmonary disease (COPD), and 291 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the blood samples of the patients with asthma or chronic obstructive pulmonary disease, as compared to that of the blood samples of the normal people (normal people vs patients with asthma: 0.7% vs 0.08%, p<0.01; normal people vs patients with chronic obstructive pulmonary disease: 0.7% vs 0.07%, p<0.01) (see FIG. 15).

Example 7

Metagenomic Analysis of Bacteria-Derived Vesicles in Clinical Samples of Patients with Inflammatory Bowel Disease Genes were extracted from vesicles present in stool samples of 57 patients with irritable bowel syndrome (IBS) and 58 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the stool samples of the patients with irritable bowel syndrome, as compared to that of the stool samples of the normal people (normal people vs patients with irritable bowel syndrome: 1.9% vs 0.00%, p<0.00001) (see FIG. 16).

In addition, genes were extracted from vesicles present in stool samples of 91 patients with inflammatory enteritis and 99 normal people as a control by using the method of Example 2, metagenomic analysis was performed thereon, and then the distribution of vesicles derived from bacteria belonging to the genus *Proteus* was evaluated. As a result, it was confirmed that the vesicles derived from bacteria belonging to the genus *Proteus* was significantly reduced in the stool samples of the patients with inflammatory enteritis, as compared to that of the stool samples of the normal people (normal people vs patients with inflammatory enteritis: 1.9% vs 0.00%, p<0.00001) (see FIG. 16).

Example 8

Isolation of Vesicles from *Proteus mirabilis* Culture Broth and Analysis of Characteristics thereof Based on the results of Examples 2 to 7, to evaluate the function of vesicles derived from bacteria belonging to the genus *Proteus*, the *Proteus mirabilis* strain, which is one species of bacteria belonging to the genus *Proteus*, was cultured and then vesicles were isolated therefrom, and characteristics of the vesicles were analyzed.

The *Proteus mirabilis* strain isolated from clinical samples of people was cultured in a brain heart infusion (BHI) medium in an anaerobic chamber at 37° C. until absorbance ($OD_{600}$) reached 1.0 to 1.5, and then subcultured. Subsequently, a *Proteus mirabilis* strain-free medium supernatant was collected and centrifuged at 10,000×g and 4° C. for 15 minutes, and the resulting supernatant was filtered using a 0.45 μm filter, and then concentrated to a volume of 200 ml through a 100 kDa hollow filter membrane by using a QuixStand benchtop system (GE Healthcare, UK). Thereafter, the concentrated supernatant was filtered again with a 0.22 μm filter. Proteins were then quantified using BCA assay, and the following experiments were performed on the obtained vesicles, and vesicles were isolated from a culture broth of *Proteus mirabilis* cultured according to the above method, and then the shape and size thereof were evaluated using an electron microscope.

As a result, as illustrated in FIG. 17A, it was confirmed that the vesicles isolated from the *Proteus mirabilis* culture broth were spherical and had a size of less than 200 nm, and it was confirmed through dynamic light scattering measurement results shown in FIG. 17B that the vesicles had a size of 37.8±13.5 nm.

Example 9

Anti-inflammatory Effect of *Proteus mirabilis*-Derived Vesicles

To examine an effect of *Proteus mirabilis*-derived vesicles on the secretion of inflammatory mediators in inflammatory cells, Raw 264.7 cells, which is a mouse macrophage line, were treated with *Proteus mirabilis*-derived vesicles (*P. mirabilis* EV) at various concentrations (0.1, 1, or 10 μg/ml), and then treated with *E. coli*-derived vesicles (*E. coli* EV), which are pathogenic vesicles, and the secretion amounts of inflammatory mediators (IL-6, TNF-α, and the like) were measured.

More specifically, Raw 264.7 cells were dispensed into a 24-well cell culture plate at a density of 1×10⁵ cells/well, and then cultured in a Dulbecco's Modified Eagle's Media (DMEM) complete medium for 24 hours. Subsequently, the culture supernatant was collected in a 1.5 ml tube and centrifuged at 3,000×g for 5 minutes, and the supernatant was collected and stored at 4° C., followed by ELISA analysis.

For ELISA analysis, the capture antibody was diluted with phosphate buffered saline (PBS) and the diluted solution was dispensed in 50 μl aliquots into a 96-well polystyrene plate in accordance with a working concentration, and then allowed to react at 4° C. overnight. Subsequently, the sample was washed twice with 100 μl of a PBST (0.05% Tween-20-containing PBS) solution, and then an RD (1% bovine serum albumin (BSA)-containing PBST) solution was dispensed in 100 μl aliquots into the plate, followed by blocking at room temperature for 1 hour and washing twice again with 100 μl of PBST, and then the sample and a standard were dispensed in 50 μl aliquots in accordance with concentration and allowed to react at room temperature for 2 hours. The sample and the standard were washed twice again with 100 μl of PBST, and then the detection antibody was diluted with RD, and the diluted solution was dispensed into 50 μl aliquots in accordance with a working concentration and allowed to react at room temperature for 2 hours. The sample and the standard were washed twice again with 100 μl of PBST, and then streptavidin-horseradish peroxidase (HRP) was diluted in RD to 1/200, and the diluted solution was dispensed in 50 μl aliquots and allowed to react at room temperature for 30 minutes. Lastly, the sample and the standard were washed three times with 100 μl of PBST, and then a solution prepared by mixing a 3,3,5,5-tetramethylbenzidine (TMB) substrate and 0.04% oxygenated water in a ratio of 1:1 was dispensed in 50 μl aliquots. Thereafter, color developing was waited for and when color was developed after 5 minutes to 20 minutes, a 1M sulfuric acid solution was dispensed in 50 μl aliquots, the reaction was stopped, and absorbance at 450 nm was measured using a Synergy™ HT multi-detection microplate reader (BioTek, USA).

As a result, it was confirmed that the secretion of IL-6 and TNF-α due to *E. coli*-derived vesicles was significantly inhibited in the case of pretreatment with *Proteus mirabilis*-derived vesicles (see FIGS. 18A and 18B).

In addition, to evaluate effects of isoforms of *Proteus mirabilis* on the anti-inflammatory effect of *Proteus mirabilis*-derived vesicles, pretreatment with vesicles derived from 5 *Proteus mirabilis* strains (PMR201, PMR202, PMR203, PMR204, and PMR205) isolated from people, at various concentrations was performed for 12 hours, followed by treatment with 1 μg/ml of *E. coli*-derived vesicles, which are pathogenic vesicles, for 12 hours. The culture supernatant was collected in a 1.5 ml tube and centrifuged at 3,000×g for 5 minutes, and the supernatant was collected and stored at 4° C., followed by ELISA analysis.

As a result, it was confirmed that similarly to the case of *Proteus mirabilis* reference strain (PMR101)-derived vesicles, the secretion of TNF-α due to *E. coli*-derived vesicles was significantly inhibited in the case of pretreatment with the vesicles derived from isolated *Proteus mirabilis* strains (see FIG. 19). In particular, it was confirmed that the inhibitory effect on the secretion of TNF-α was greater in the case of pretreatment with *Proteus mirabilis*-derived vesicles than in the case of vesicles derived from *Lactobacillus plantarum*, which is an effective microorganism control (see FIG. 19).

This indicates that vesicles derived from isolated *Proteus mirabilis* strains were able to efficiently inhibit inflammatory responses induced by pathogenic vesicles such as *E. coli*-derived vesicles, regardless of isoforms thereof.

Example 10

Effect of Heat-Treated or Acid-Treated *Proteus mirabilis*-Derived Vesicles on Anti-Inflammatory Activity Through Example 9, the anti-inflammatory effects of vesicles derived from the *Proteus mirabilis* reference strain and isolated *Proteus mirabilis* strains were confirmed, and further, the stability of the vesicles and properties of the active ingredient were specifically investigated. For this, macrophages (Raw 264.7) were pretreated with three types of *Proteus mirabilis*-derived vesicles (PMR101, PMR202, and PMR205) that had been boiled at 100° C. for 10 minutes or subjected to acid treatment (pH 2.0) for 10 minutes to evaluate anti-inflammatory effects thereof.

As a result, it was confirmed that the anti-inflammatory effects of the *Proteus mirabilis*-derived vesicles were maintained even after boiling at 100° C. or acid treatment (see FIG. 20). This indicates that *Proteus mirabilis*-derived vesicles are stable at a high temperature and a high acid level, and this also indicates that a component of *Proteus mirabilis*-derived vesicles which exhibits an anti-inflammatory effect is not a protein.

Example 11

Anticancer Effect of *Proteus mirabilis*-Derived Vesicles

Through the above examples, vesicles derived from bacteria belonging to the genus *Proteus* was significantly reduced in clinical samples of patients with cancer, as compared to that of normal people, and further, an anticancer effect of the vesicles was specifically investigated. For this, as depicted in FIG. 21A, cancer models were prepared by orally administering *Proteus mirabilis*-derived vesicles to male 6-week-old C57BL/6 mice and subcutaneously injecting a cancer cell line (CT26 cells) into the mice on day 4 after administration. Until day 20 after the cancer cell line was administered, the size of cancer tissue was measured to evaluate cancer therapeutic effects. As a result, the size of cancer tissue was significantly reduced in the mice orally administered the vesicles, as compared to that of a group orally administered normal saline (see FIG. 21B).

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation.

INDUSTRIAL APPLICABILITY

Vesicles derived from bacteria belonging to the genus *Proteus*, according to the present invention, can be used in a method of diagnosing various diseases, such as cancers such as stomach cancer, colorectal cancer, liver cancer, bile duct cancer, pancreatic cancer, lung cancer, breast cancer, ovarian cancer, bladder cancer, prostate cancer, lymphoma, a brain tumor, and the like; cardiovascular diseases such as myocardial infarction, cardiomyopathy, atrial fibrillation, variant angina, a stroke, and the like; metabolic diseases such as diabetes, and the like; neuropsychiatric diseases such as Parkinson's disease, depression, and the like; allergic-respiratory diseases such as atopic dermatitis, asthma, chronic obstructive pulmonary disease, and the like; or inflammatory bowel diseases such as irritable bowel syndrome, inflammatory enteritis, and the like, and thus it is economical and it is anticipated that the vesicles can be applied to various applications such as compositions for prevention, treatment, and/or alleviation, e.g., foods, inhalants, cosmetic, drugs, and the like. Therefore, the vesicles can be usefully used in various industrial fields such as medical, functional food, and cosmetic industries.

The invention claimed is:

1. A method of alleviating or treating colorectal cancer comprising administering to a subject in need thereof a composition comprising an effective amount of vesicles isolated from bacteria belonging to *Proteus mirabilis*, wherein the vesicles themselves are an active ingredient and the vesicles comprise naturally occurring vesicles secreted by *Proteus mirabilis*.

2. The method of claim 1, wherein the composition is a pharmaceutical composition, a food composition, or a cosmetic composition.

3. The method of claim 1, wherein the vesicles have an average diameter of 10 nm to 200 nm.

4. The method of claim 1, wherein the composition is an inhalant composition.

* * * * *